United States Patent

Fischer et al.

Patent Number: 6,051,723
Date of Patent: Apr. 18, 2000

[54] 3-ARYL-TETRONIC ACID DERIVATIVES

[75] Inventors: Reiner Fischer, Monheim; Thomas Bretschneider, Lohmar; Gunther Beck; Hermann Hagemann, both of Leverkusen; Christoph Erdelen, Leichlingen; Ulrike Wachendorff-Neumann, Neuwied; Wolfram Andersch, Bergisch Gladbach; Norbert Mencke, Leverkusen; Andreas Turberg, Erkrath, all of Germany

[73] Assignee: Bayer Aktiengesellschaft, Leverkusen, Germany

[21] Appl. No.: 09/133,522

[22] Filed: Aug. 13, 1998

Related U.S. Application Data

[62] Division of application No. 08/860,106, filed as application No. PCT/EP95/04869, Dec. 11, 1995, Pat. No. 5,830,825.

[30] Foreign Application Priority Data

Dec. 23, 1994 [DE] Germany .............................. 44 46 335
Nov. 2, 1995 [DE] Germany ............................ 195 40 736

[51] Int. Cl.$^7$ ...................... C07D 309/10; C07D 307/24
[52] U.S. Cl. .......................... 549/420; 549/28; 549/475; 546/227; 548/531
[58] Field of Search .......................... 546/227; 548/531; 549/28, 420, 475

[56] References Cited

U.S. PATENT DOCUMENTS 5,262,383  11/1993  Fischer et al. ............................ 504/195

FOREIGN PATENT DOCUMENTS

| 0 528 156 | 2/1993 | European Pat. Off. . |
| 0 647 637 | 4/1995 | European Pat. Off. . |
| 0 668 267 | 8/1995 | European Pat. Off. . |
| 92 589 | 5/1896 | Germany . |
| 3 913 757 | 10/1990 | Germany . |
| WO 95 01971 | 1/1995 | WIPO . |

OTHER PUBLICATIONS

Nazarov et al., The Journal of General Chemnistry of the U.S.S.R., Oct. 1956, vol. 26, No. 10, pp. 3891–3898.
Unkovskii et al., Journal of General Chemistry of the USSR, Dec. 1960, vol. 30, No. 12, pp. 3883–3887.

*Primary Examiner*—Bernard Dentz
*Attorney, Agent, or Firm*—Norris, McLaughlin & Marcus, P.A.

[57] ABSTRACT

The present invention relates to new 3-aryl-4-hydroxy-Δ$^3$-dihydrofuranone derivatives of the formula (I)

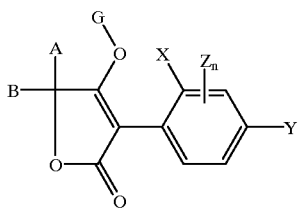

(I)

in which

A and B together with the carbon atom to which they are bonded form an unsubstituted or substituted 5- to 7-membered ring which is interrupted by at least one hetero atom, X represents alkyl, halogen or alkoxy, Y represents hydrogen, alkyl, halogen, alkoxy or halogenoalkyl, Z represents alkyl, halogen or alkoxy, n represents a number 0, 1, 2 or 3, G represents hydrogen (a) or one of the groups

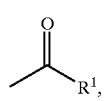
(b)

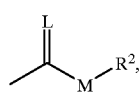

(c)

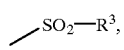

(d)

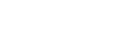

(e)

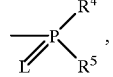

(f)

E or

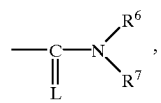
(g)

E represents a metal ion equivalent or an ammonium ion,

L represents oxygen or sulphur,

M represents oxygen or sulphur and $R^1$, $R^2$, $R^3$, $R^4$, $R^5$, $R^6$ and $R^7$ have the meanings given in the description, to processes for their preparation, and to their use as pesticides.

2 Claims, No Drawings

3-ARYL-TETRONIC ACID DERIVATIVES

This application is a divisional of application Ser. No. 08/860,106, filed on Jun. 17, 1997 now U.S. Pat. No. 5,830,825, which is a 371 of PCT/EP95/04869 filed Dec. 11, 1995.

The present invention relates to new 3-aryl-4-hydroxy-$\Delta^3$-dihydro-furanone derivatives (3-aryl-tetronic acid derivatives), to processes for their preparation, and to their use as pesticides.

It has been disclosed that certain substituted $\Delta^3$-dihydrofuran-2-one derivatives have herbicidal properties (cf. DE-A-4 014 420). The synthesis of the tetronic acid derivatives used as starting compounds (such as, for example, 3-(2-methyl-phenyl)-4-hydroxy-5-(4-fluorophenyl)-$\Delta^3$-dihydrofuran-2-one) is also described in DE-A-4 014 420. Compounds of a similar structure are known from the publication of Campbell et al., J. Chem. Soc., Perkin Trans. 1, 1985, (8) 1567–76, without an insecticidal and/or acaricidal activity being mentioned. Furthermore, 3-aryl-$\Delta^3$-dihydrofuranone derivatives having herbicidal, acaricidal and insecticidal properties are disclosed in EP-528 156, but the action described therein is not always sufficient.

There have now been found new 3-aryl-4-hydroxy-$\Delta^3$-dihydrofuranone derivatives of the formula (I)

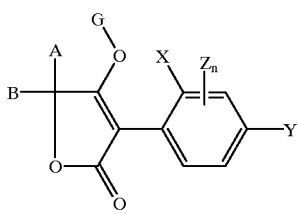
(I)

in which

A and B together with the carbon atom to which they are bonded form an unsubstituted or substituted 5- to 7-membered ring which is interrupted by at least one hetero atom, X represents alkyl, halogen or alkoxy, Y represents hydrogen, alkyl, halogen, alkoxy or halogenoalkyl, Z represents alkyl, halogen or alkoxy, n represents a number 0, 1, 2 or 3, G represents hydrogen (a) or one of the groups

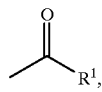
(b)

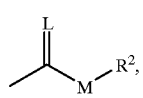
(c)

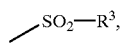
(d)

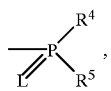
(e)

E or (f)

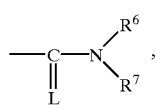
(g)

E represents a metal ion equivalent or an ammonium ion,

L represents oxygen or sulphur,

M represents oxygen or sulphur, $R^1$ represents alkyl, alkenyl, alkoxyalkyl, alkylthioalkyl, polyalkoxyalkyl, each of which is optionally substituted by halogen, or represents cycloalkyl which can be interrupted by at least one hetero atom and which is optionally substituted by halogen, alkyl or alkoxy, or represents in each case optionally substituted phenyl, phenylalkyl, hetaryl, phenoxyalkyl or hetaryloxyalkyl, $R^2$ represents alkyl, alkenyl, alkoxyalkyl or polyalkoxyalkyl, each of which is optionally substituted by halogen, or represents cycloalkyl which is optionally substituted by halogen, alkoxy or alkyl, or represents in each case optionally substituted phenyl or benzyl, $R^3$, $R^4$ and $R^5$ independently of one another represent alkyl, alkoxy, alkylamino, dialkylamino, alkylthio, alkenylthio or cycloalkylthio, each of which is optionally substituted by halogen, or represent in each case optionally substituted phenyl, benzyl, phenoxy or phenylthio, and $R^6$ and $R^7$ independently of one another represent hydrogen, or represent alkyl, cycloalkyl, alkenyl, alkoxy or alkoxyalkyl, each of which is optionally substituted by halogen, or represent in each case optionally substituted phenyl or benzyl, or together represent an alkanediyl radical which is optionally interrupted by oxygen or sulphur.

Taking into consideration the various meanings (a), (b), (c), (d), (e), (f) and (g) of group G, the following main structures (Ia) to (Ig) result:

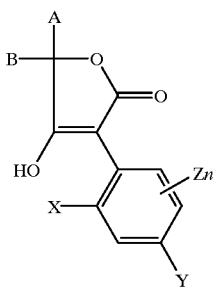
(Ia)

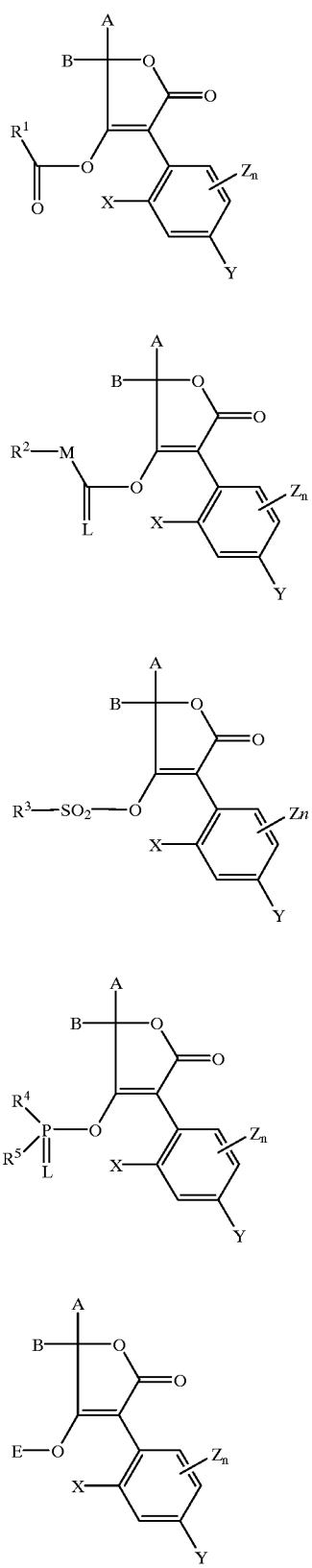

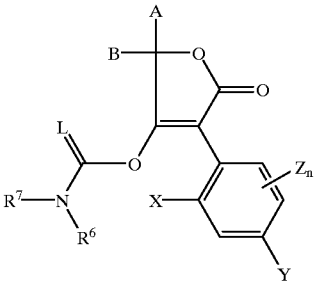

in which

A, B, E, L, M, X, Y, Z, $R^1$, $R^2$, $R^3$, $R^4$, $R^5$, $R^6$, $R^7$ and n have the abovementioned meanings.

Due to one or more chiral centres, the compounds of the formulae (Ia) to (Ig) are generally obtained in the form of a stereoisomer mixture. They can be used in the form of their diastereomer mixtures, but also in the form of pure diastereomers or enantiomers.

Furthermore, it has been found that the new substituted 3-aryl-tetronic acid derivatives of the formula (I) are obtained by one of the processes described hereinbelow.

(A) 3-Aryl-tetronic acids of the formula (Ia)

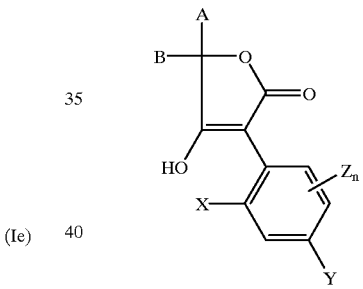

in which

A, B, X, Y, Z and n have the abovementioned meanings, are obtained when carboxylic esters of the formula (II)

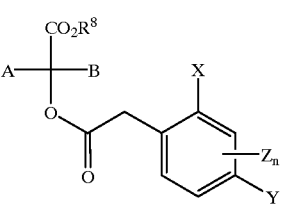

in which

A, B, X, Y, Z and n have the abovementioned meanings and $R^8$ represents alkyl, preferably $C_1$–$C_8$-alkyl, are subjected to an intramolecular condensation reaction in the presence of a diluent and in the presence of a base; and (B) compounds of the formula (Ib)

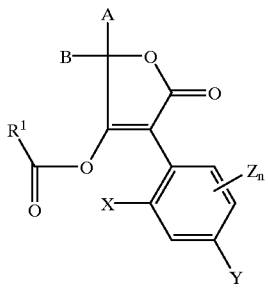
(Ib)

in which

A, B, X, Y, Z, $R^1$ and n have the abovementioned meanings, are obtained when compounds of the formula (Ia)

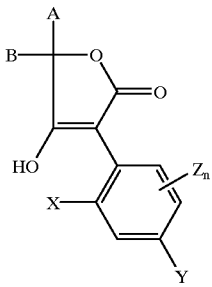
(Ia)

in which

A, B, X, Y, Z and n have the abovementioned meanings, are reacted

α) with acid halides of the formula (III)

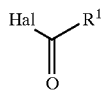
(III)

in which $R^1$ has the abovementioned meanings and

Hal represents halogen, in particular chlorine and bromine, if appropriate in the presence of a diluent and if appropriate in the presence of an acid-binding agent, or β) with carboxylic anhydrides of the formula (IV)

$R^1$—CO—O—CO—$R^1$     (IV)

in which $R^1$ has the abovementioned meanings, if appropriate in the presence of a diluent and if appropriate in the presence of an acid-binding agent; and (C) compounds of the formula (Ic-1)

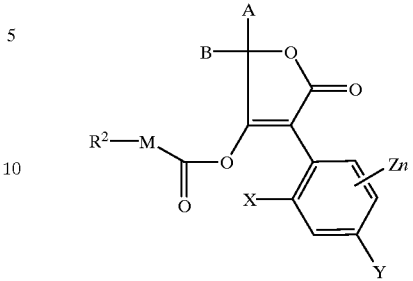
(Ic-1)

in which

A, B, X, Y, Z, $R^2$ and n have the abovementioned meanings and

M represents oxygen or sulphur, are obtained when compounds of the formula (Ia)

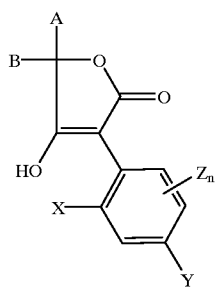
(Ia)

in which

A, B, X, Y, Z and n have the abovementioned meanings, are reacted with chloroformic esters or chloroformic thioesters of the formula (V)

$R^2$—M—CO—Cl     (V)

in which $R^2$ and M have the abovementioned meanings, if appropriate in the presence of a diluent and if appropriate in the presence of an acid-binding agent; and (D) compounds of the formula (Ic-2)

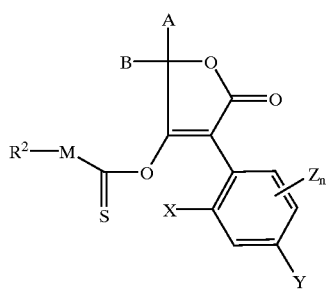
(Ic-2)

in which

A, B, $R^2$, X, Y, Z and n have the abovementioned meanings and

M represents oxygen or sulphur are obtained when compounds of the formula (Ia)

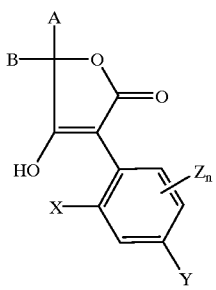

(Ia)

in which

A, B, X, Y, Z and n have the abovementioned meanings, are reacted

α) with chloromonothioformic esters or chlorodithioformic esters of the formula (VI)

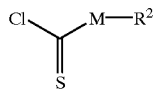

(VI)

in which

M and $R^2$ have the abovementioned meanings, if appropriate in the presence of a diluent and if appropriate in the presence of an acid-binding agent, or β) with carbon disulphide and then with alkyl halides of the formula (VII)

$R^2$—Hal  (VII)

in which $R^2$ has the abovementioned meanings and

Hal represents chlorine, bromine or iodine, if appropriate in the presence of a diluent and if appropriate in the presence of a base; and (E) compounds of the formula (Id)

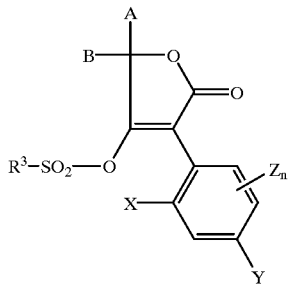

(Id)

in which

A, B, X, Y, Z, $R^3$ and n have the abovementioned meanings, are obtained when compounds of the formula (Ia)

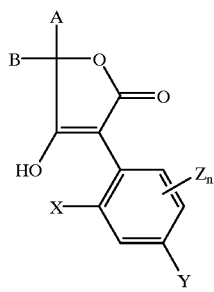

(Ia)

in which

A, B, X, Y, Z and n have the abovementioned meanings, are reacted with sulphonyl chlorides of the formula (VIII)

$R^3$—$SO_2$—Cl  (VIII)

in which $R^3$ has the abovementioned meanings, if appropriate in the presence of a diluent and if appropriate in the presence of an acid-binding agent; and (F) compounds of the formula (Ie)

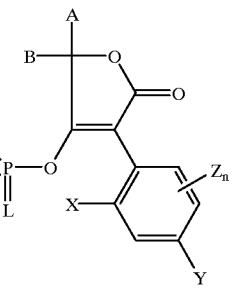

(Ie)

in which

A, B, L, X, Y, Z, $R^4$, $R^5$ and n have the abovementioned meanings, are obtained when compounds of the formula (Ia)

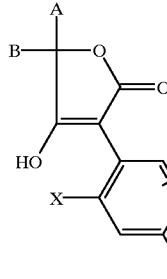

(Ia)

in which

A, B, X, Y, Z and n have the abovementioned meanings, are reacted with phosphorus compounds of the formula (IX)

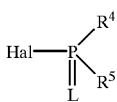

(IX)

in which

L, $R^4$ and $R^5$ have the abovementioned meanings and

Hal represents halogen, in particular chlorine and bromine, if appropriate in the presence of a diluent and if appropriate in the presence of an acid-binding agent; and (G) compounds of the formula (If)

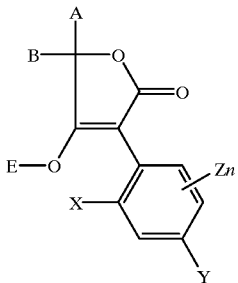

(IX)

in which

A, B, X, Y, Z and n have the abovementioned meanings and

E represents a metal ion equivalent or an ammonium ion are obtained when compounds of the formula (Ia)

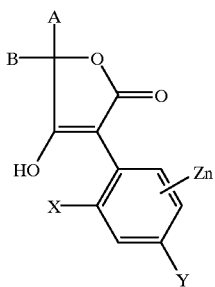

(Ia)

in which

A, B, X, Y, Z and n have the abovementioned meanings, are reacted with metal compounds or amines of the formulae (X) or (XI)

MeR$^{13}{}_t$ (X)

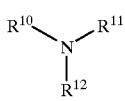

(XI)

in which

Me represents mono- or divalent metal ions, for example alkali metal or alkaline earth metal ions, such as, for example, Li$^+$, Na$^+$, K$^+$, Ca$^{2+}$ or Mg$^{2+}$, t represents the number 1 or 2, $R^{10}$, $R^{11}$ and $R^{12}$ independently of one another represent hydrogen or alkyl (in particular $C_1$–$C_8$-alkyl) and $R^{13}$ represents hydrogen, hydroxyl or $C_1$–$C_4$-alkoxy, if appropriate in the presence of a diluent.

(H) Furthermore, it has been found that compounds of the formula (I-g)

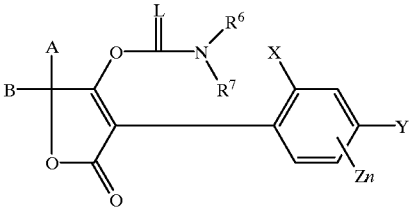

(Ig)

in which

A, B, L, X, Y, Z, $R^6$, $R^7$ and n have the abovementioned meanings, are obtained when compounds of the formula (Ia)

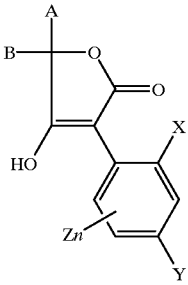

(Ia)

in which

A, B, X, Y, Z and n have the abovementioned meanings, are reacted

α) with compounds of the formula (XII)

$R^6$—N=C=L (XII)

in which

L and $R^6$ have the abovementioned meanings, if appropriate in the presence of a diluent and if appropriate in the presence of a catalyst, or β) with carbamoyl chlorides or thiocarbamoyl chlorides of the formula (XIII)

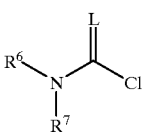

(XIII)

in which

L, $R^6$ and $R^7$ have the abovementioned meanings, if appropriate in the presence of a diluent and if appropriate in the presence of an acid-binding agent.

Furthermore, it has been found that the new compounds of the formula (I) are distinguished by outstanding insecticidal and acaricidal actions. Preferred substituents or ranges of the radicals listed in the formulae mentioned hereinabove and hereinbelow are illustrated in the following text.

A and B preferably represent $C_4$–$C_6$-alkanediyl which is optionally monosubstituted or polysubstituted by identical or different substituents from the series consisting of halogen, $C_1$–$C_8$-alkyl, $C_3$–$C_8$-cycloalkyl, $C_1$–$C_8$-halogenoalkyl, $C_1$–$C_6$-alkoxy, $C_1$–$C_6$-alkylthio or phenyl and in which one or two carbon atoms which are not directly adjacent are replaced by the group

and/or oxygen and/or sulphur.

A and B particularly preferably represent $C_4$–$C_5$-alkanediyl which is optionally monosubstituted to tetrasubstituted by identical or different substituents from the series consisting of fluorine, chlorine, $C_1$–$C_6$-alkyl, $C_3$–$C_6$-cycloalkyl, $C_1$–$C_6$-halogenoalkyl, $C_1$–$C_4$-alkoxy, $C_1$–$C_4$-alkylthio or phenyl and in which one or two carbon atoms which are not directly adjacent are replaced by the group

or by oxygen or by sulphur.

A and B very particularly preferably represent $C_4$–$C_5$-alkanediyl which is optionally monosubstituted to trisubstituted by identical or different substituents from the series consisting of fluorine, chlorine, methyl, ethyl, n-propyl, i-propyl, n-butyl, i-butyl, sec-butyl, tert-butyl, cyclohexyl, trifluoromethyl, methoxy, methylthio or phenyl and in which one carbon atom is replaced by the group

or by oxygen or by sulphur.

X preferably represents $C_1$–$C_6$-alkyl, halogen or $C_1$–$C_6$-alkoxy.

X particularly preferably represents $C_1$–$C_4$-alkyl, fluorine, chlorine, bromine or $C_1$–$C_4$-alkoxy.

X very particularly preferably represents methyl, ethyl, n-propyl, iso-propyl, fluorine, chlorine, bromine, methoxy or ethoxy.

Y preferably represents hydrogen, $C_1$–$C_6$-alkyl, halogen, $C_1$–$C_6$-alkoxy or $C_1$–$C_3$-halogenoalkyl.

Y particularly preferably represents hydrogen, $C_1$–$C_4$-alkyl, fluorine, chlorine, bromine, $C_1$–$C_4$-alkoxy or $C_1$–$C_2$-halogenoalkyl.

Y very particularly preferably represents hydrogen, methyl, ethyl, n-propyl, i-propyl, n-butyl, i-butyl, tert-butyl, fluorine, chlorine, bromine, methoxy, ethoxy or trifluoromethyl.

Z preferably represents $C_1$–$C_6$-alkyl, halogen or $C_1$–$C_6$-alkoxy.

Z particularly preferably represents $C_1$–$C_4$-alkyl, fluorine, chlorine, bromine or $C_1$–$C_4$-alkoxy.

Z very particularly preferably represents methyl, ethyl, propyl, i-propyl, n-butyl, i-butyl, tert-butyl, fluorine, chlorine, bromine, methoxy or ethoxy.

G preferably represents hydrogen (a) or one of the groups

(b)

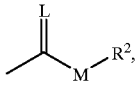
(c)

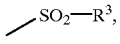
(d)

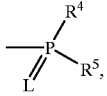
(e)

E or
(f)

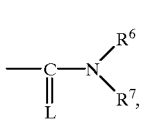
(g)

in which
E represents a metal ion equivalent or an ammonium ion,
L represents oxygen or sulphur and
M represents oxygen or sulphur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_2$–$C_8$-alkyl, each of which is optionally monosubstituted or polysubstituted by halogen, or represents $C_3$–$C_8$-cycloalkyl which is optionally substituted by halogen, $C_1$–$C_6$-alkyl or $C_1$–$C_6$-alkoxy and in which one or two methylene groups which are not directly adjacent are optionally replaced by oxygen and/or sulphur, or represents phenyl which is optionally monosubstituted to pentasubstituted by halogen, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, or represents phenyl-$C_1$–$C_6$-alkyl which is optionally monosubstituted to pentasubstituted by halogen, $C_1$–$C_6$-alkyl, $C_1$–$C_6$-alkoxy, $C_1$–$C_6$-halogenoalkyl or $C_1$–$C_6$-halogenoalkoxy,
or represents pyridyl, thienyl, furanyl, pyrazolyl, pyrimidyl or thiazolyl, each of which is optionally monosubstituted or disubstituted by halogen or $C_1$–$C_6$-alkyl,
or represents phenoxy-$C_1$–$C_6$-alkyl which is optionally monosubstituted to trisubstituted by halogen or $C_1$–$C_6$-alkyl,
or represents pyridinyloxy-$C_1$–$C_6$-alkyl, pyrimidinyloxy-$C_1$–$C_6$-alkyl or thiazolyloxy-$C_1$–$C_6$-alkyl, each of which is optionally monosubstituted or disubstituted by halogen, amino or $C_1$–$C_6$-alkyl.

$R^2$ preferably represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally monosubstituted or polysubstituted by halogen,
or represents $C_3$–$C_8$-cycloalkyl which is optionally monosubstituted or polysubstituted by halogen, $C_1$–$C_4$-alkyl or $C_1$–$C_4$-alkoxy,
or represents phenyl or benzyl, each of which is optionally monosubstituted to trisubstituted by halogen, nitro, $C_1$–$C_6$-alkyl, $C_1$–$C_6$-alkoxy or $C_1$–$C_6$-halogenoalkyl.

$R^3$ preferably represents $C_1$–$C_8$-alkyl which is optionally monosubstituted or polysubstituted by halogen, or represents phenyl or benzyl, each of which is optionally monosubstituted or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^4$ and $R^5$ independently of one another preferably represent $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_3$–$C_6$-alkenylthio or $C_3$–$C_7$-cycloalkylthio, each of which is optionally monosubstituted or polysubstituted by halogen, or represent phenyl, phenoxy or phenylthio, each of which is optionally monosubstituted or polysubstituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another preferably represent hydrogen, or represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_1$–$C_8$-alkyl, each of which is optionally monosubstituted or polysubstituted by halogen, or represent phenyl or benzyl, each of which is optionally monosubstituted to trisubstituted by halogen, $C_1$–$C_8$-alkyl, $C_1$–$C_8$-halogenoalkyl or $C_1$–$C_8$-alkoxy, or together represent a $C_2$–$C_6$-alkanediyl radical which is optionally interrupted by oxygen or sulphur.

$R^9$ preferably represents hydrogen, Q, COQ or $CO_2Q$, where

Q can assume the meanings which have been mentioned above as being preferred for $R^2$.

n preferably represents 0, 1 or 2.

G particularly preferably represents hydrogen (a) or one of the groups

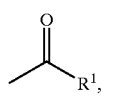 (b)

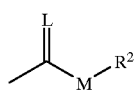 (c)

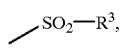 (d)

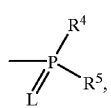 (e)

E or (f)

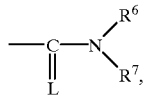 (g)

in which
E represents a metal ion equivalent or an ammonium ion,
L represents oxygen or sulphur and
M represents oxygen or sulphur.

$R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl, each of which is optionally monosubstituted to hexasubstituted by fluorine or chlorine, or represents $C_3$–$C_7$-cycloalkyl which is optionally substituted by fluorine, chlorine, $C_1$–$C_5$-alkyl or $C_1$–$C_5$-alkoxy and in which one or two methylene groups which are not directly adjacent are optionally replaced by oxygen and/or sulphur, or represents phenyl which is optionally monosubstituted to trisubstituted by fluorine, chlorine, bromine, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, or represents phenyl-$C_1$–$C_4$-alkyl which is optionally monosubstituted to trisubstituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or represents pyridyl, thienyl, furanyl, pyrazolyl, pyrimidyl or thiazolyl, each of which is optionally monosubstituted or disubstituted by fluorine, chlorine, bromine or $C_1$–$C_4$-alkyl, or represents phenoxy-$C_1$–$C_5$-alkyl which is optionally monosubstituted or disubstituted by fluorine, chlorine, bromine or $C_1$–$C_4$-alkyl, or represents pyrimidinyloxy-$C_1$–$C_5$-alkyl, pyridinyloxy-$C_1$–$C_5$-alkyl or thiazolyloxy-$C_1$–$C_5$-alkyl, each of which is optionally monosubstituted or disubstituted by fluorine, chlorine, bromine, amino or $C_1$–$C_4$-alkyl.

$R^2$ particularly preferably represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, each of which is optionally monosubstituted to hexasubstituted by fluorine or chlorine, or represents $C_3$–$C_7$-cycloalkyl which is optionally monosubstituted to hexasubstituted by fluorine, chlorine, $C_1$–$C_3$-alkyl or $C_1$–$C_3$-alkoxy, or represents phenyl or benzyl, each of which is optionally monosubstituted or disubstituted by fluorine, chlorine, bromine, nitro, $C_1$–$C_4$-alkyl, $C_1$–$C_3$-alkoxy or $C_1$–$C_3$-halogenoalkyl.

$R^3$ particularly preferably represents $C_1$–$C_6$-alkyl which is optionally monosubstituted to hexasubstituted by fluorine or chlorine, or represents phenyl or benzyl, each of which is optionally monosubstituted or disubstituted by fluorine, chlorine, bromine, $C_1$–$C_5$-alkyl, $C_1$–$C_5$-alkoxy, $C_1$–$C_3$-halogenoalkyl, $C_1$–$C_3$-halogenoalkoxy, cyano or nitro.

$R^4$ and $R^5$ independently of one another particularly preferably represent $C_1$–$C_6$-alkyl, $C_1$–$C_6$-alkoxy, $C_1$–$C_6$-alkylamino, di-($C_1$–$C_6$)-alkylamino, $C_1$–$C_6$-alkylthio, $C_3$–$C_4$-alkenylthio or $C_3$–$C_6$-cycloalkylthio, each of which is optionally monosubstituted to hexasubstituted by fluorine or chlorine, or represent phenyl, phenoxy or phenylthio, each of which is optionally monosubstituted or disubstituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, or represent $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_1$–$C_6$-alkyl, each of which is optionally monosubstituted to hexasubstituted by fluorine or chlorine, or represent phenyl or benzyl, each of which is optionally monosubstituted or disubstituted by fluorine, chlorine, bromine, $C_1$–$C_5$-alkyl, $C_1$–$C_5$-halogenoalkyl or $C_1$–$C_5$-alkoxy, or together represent a $C_2$–$C_6$-alkanediyl radical which is optionally interrupted by oxygen or sulphur.

$R^9$ particularly preferably represents hydrogen, Q, COQ or $CO_2Q$,
where
Q represents $C_1$–$C_6$-alkyl, phenyl or benzyl.

n particularly preferably represents 0 or 1.

G very particularly preferably represents hydrogen (a) or one of the groups

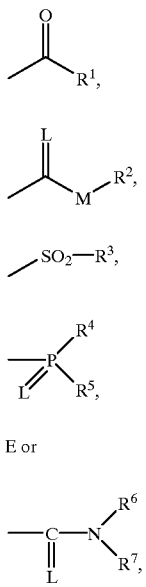

(b)

(c)

(d)

(e)

(f) E or (g)

in which

E represents a metal ion equivalent or an ammonium ion,

L represents oxygen or sulphur and

M represents oxygen or sulphur.

$R^1$ very particularly preferably represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or poly-$C_1$–$C_4$-alkoxy-$C_1$–$C_4$-alkyl, each of which is optionally monosubstituted to trisubstituted by fluorine or chlorine, or represents $C_3$–$C_6$-cycloalkyl which is optionally substituted by fluorine, chlorine, methyl, ethyl, propyl, i-propyl, butyl, i-butyl, t-butyl, methoxy, ethoxy, propoxy, i-propoxy, butoxy, i-butoxy, s-butoxy or t-butoxy and in which one methylene group is optionally replaced by oxygen or sulphur, or represents phenyl which is optionally monosubstituted or disubstituted by fluorine, chlorine, bromine, methyl, ethyl, propyl, i-propyl, methoxy, ethoxy, trifluoromethyl, trifluoromethoxy, methylthio, ethylthio, methylsulphonyl, ethylsulphonyl or nitro, or represents phenyl-$C_1$–$C_3$-alkyl which is optionally monosubstituted or disubstituted by fluorine, chlorine, bromine, methyl, ethyl, propyl, i-propyl, methoxy, ethoxy, trifluoromethyl or trifluoromethoxy, or represents thienyl, furanyl or pyridyl, each of which is optionally monosubstituted or disubstituted by fluorine, chlorine, bromine, methyl or ethyl, or represents phenoxy-$C_1$–$C_4$-alkyl which is optionally monosubstituted or disubstituted by fluorine, chlorine, methyl or ethyl, or represents pyridyloxy-$C_1$–$C_4$-alkyl, pyrimidyloxy-$C_1$–$C_4$-alkyl or thiazolyloxy-$C_1$–$C_4$-alkyl, each of which is optionally monosubstituted or disubstituted by fluorine, chlorine, amino, methyl or ethyl.

$R^2$ very particularly preferably represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, each of which is optionally monosubstituted to trisubstituted by fluorine or chlorine, or represents $C_3$–$C_6$-cycloalkyl which is optionally monosubstituted to trisubstituted by fluorine, chlorine, methyl, ethyl, propyl, iso-propyl or methoxy, or represents phenyl or benzyl, each of which is optionally monosubstituted or disubstituted by fluorine, chlorine, nitro, methyl, ethyl, propyl, i-propyl, methoxy, ethoxy or trifluoromethyl.

$R^3$ very particularly preferably represents methyl, ethyl, propyl or isopropyl, each of which is optionally monosubstituted to trisubstituted by fluorine or chlorine, or represents phenyl or benzyl, each of which is optionally monosubstituted or disubstituted by fluorine, chlorine, bromine, methyl, ethyl, propyl, iso-propyl, tert-butyl, methoxy, ethoxy, isopropoxy, tertbutoxy, trifluoromethyl, trifluoromethoxy, cyano or nitro.

$R^4$ and $R^5$ independently of one another very particularly preferably represent $C_1$–$C_4$-alkyl, $C_1$–$C_4$-alkoxy, $C_1$–$C_4$-alkylamino, di-($C_1$–$C_4$)-alkylamino or $C_1$–$C_4$-alkylthio, each of which is optionally monosubstituted to trisubstituted by fluorine or chlorine, or represent phenyl, phenoxy or phenylthio, each of which is optionally monosubstituted or disubstituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio, $C_1$–$C_2$-alkyl or $C_1$–$C_2$-fluoroalkyl.

$R^6$ and $R^7$ independently of one another very particularly preferably represent hydrogen, or represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_1$–$C_4$-alkyl, each of which is optionally monosubstituted to trisubstituted by fluorine or chlorine, or represent phenyl or benzyl, each of which is optionally monosubstituted or disubstituted by fluorine, chlorine, bromine, $C_1$–$C_4$-alkyl, $C_1$–$C_4$-halogenoalkyl or $C_1$–$C_4$-alkoxy, or together represent a $C_2$–$C_6$-alkanediyl radical which is optionally interrupted by oxygen or sulphur.

$R^9$ very particularly preferably represents hydrogen, Q, COQ or $CO_2Q$, where Q represents $C_1$–$C_4$-alkyl, phenyl or benzyl.

n very particularly preferably represents 0 or 1.

In the definitions given, saturated or unsaturated hydrocarbon radicals, also in connection with hetero atoms such as, for example, alkoxy or alkylthio, can, wherever possible, be straight-chain or branched.

The optionally polysubstituted radicals can be substituted by the identical or different substituents mentioned for these radicals.

The abovementioned definitions of radicals or illustrations, in general or in preferred ranges, can be combined with each other as desired, that is to say combinations between the respective ranges and preferred ranges are also possible. They apply to the end products and, correspondingly, to the precursors and intermediates.

Preferred according to the invention are those compounds of the formula (I) in which there exists a combination of the meanings mentioned above as being preferred (preferable).

Particularly preferred according to the invention are those compounds of the formula (I) in which there exists a combination of the meanings mentioned above as being particularly preferred.

Very particularly preferred according to the invention are those compounds of the formula (I) in which there exists a combination of the meanings mentioned above as being very particularly preferred.

A preferred group of compounds are those compounds of the formula (I) in which n represents the number 1 and the substituent Z is in the 6-position of the phenyl radical.

A further preferred group of compounds are those compounds of the formula (I) in which n represents the number 0 and Y simultaneously does not represent hydrogen.

Another preferred group of compounds are those compounds of the formula (I) in which n represents the number 1 and Y simultaneously represents hydrogen.

In addition to the compounds mentioned in the Preparation Examples, the compounds of the formula (Ia) listed in Tables 1 to 4 below may be mentioned individually:

TABLE 1

(Ia)

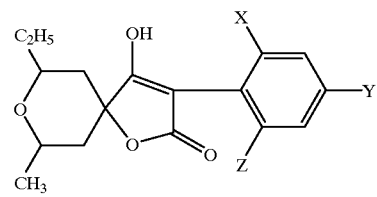

| X | Y | Z |
|---|---|---|
| CH₃ | CH₃ | H |
| Cl | Cl | H |
| CH₃ | Cl | H |
| Cl | CH₃ | H |
| CH₃ | OCH₃ | H |
| OCH₃ | CH₃ | H |
| Cl | OCH₃ | H |
| OCH₃ | Cl | H |
| OCH₃ | OCH₃ | H |
| Cl | H | Cl |
| Cl | H | F |
| Cl | H | OCH₃ |
| CH₃ | H | CH₃ |
| CH₃ | H | OCH₃ |
| CH₃ | H | Cl |
| OCH₃ | H | OCH₃ |
| CH₃ | CH₃ | CH₃ |
| CH₃ | CH₃ | OCH₃ |
| CH₃ | OCH₃ | CH₃ |
| Cl | Cl | Cl |
| Cl | CF₃ | Cl |

Table 2 contains the compounds of the formula

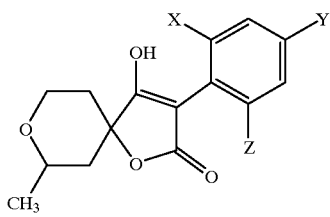

in which X, Y and Z have the meanings given in Table 1.

Table 3 contains the compounds of the formula

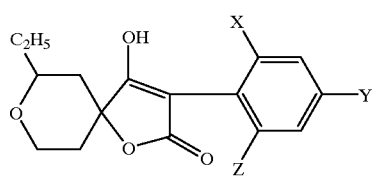

in which X, Y and Z have the meanings given in Table 1.

Table 4 contains the compounds of the formula

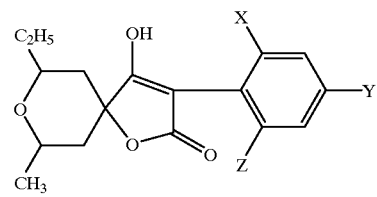

in which X, Y and Z have the meanings given in Table 1.

If, in accordance with process (A), ethyl 1-(2,4-dichlorophenylacetyloxy)-4-oxacyclohexane-carboxylate is used, the course of the process according to the invention can be represented by the following equation:

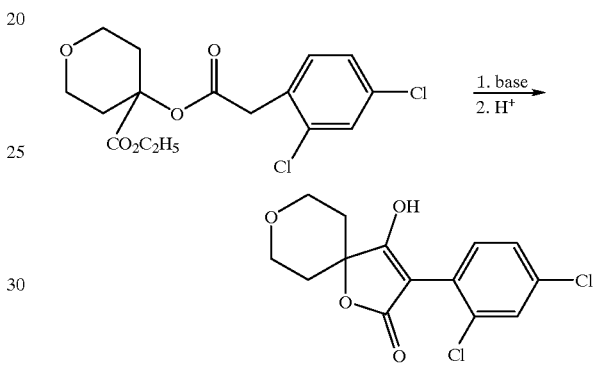

If, in accordance with process (B) (Variant α), 3-(2,4,6-trimethylphenyl)-5,5-(ethyleneoxaethylene)-tetronic acid and pivaloyl chloride are used as starting substances, the course of the process according to the invention can be represented by the following equation:

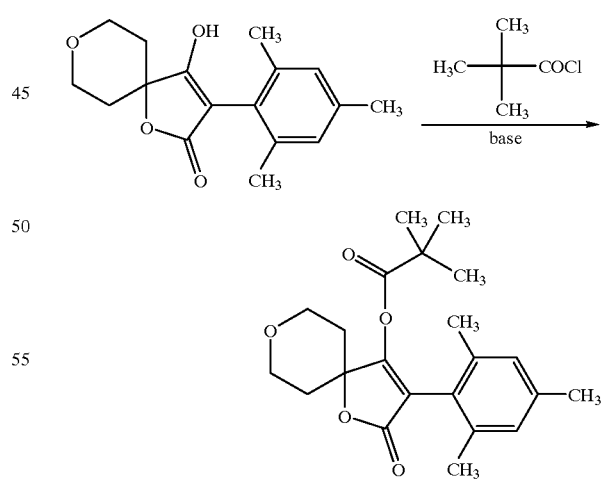

If, in accordance with process (B) (Variant β), 3-(2,4,6-trimethylphenyl)-5,5-ethyleneoxamethylene-tetronic acid and acetic anhydride are used as starting compounds, the course of the process according to the invention can be represented by the following equation:

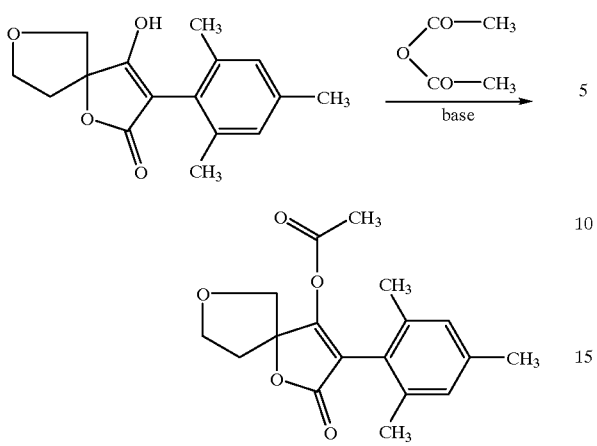

If, in accordance with process (C), 3-(2,4,6-trimethylphenyl)-5,5-ethyleneoxamethylene-tetronic acid and ethoxyethyl chloroformate are used as starting compounds, the course of the process according to the invention can be represented by the following equation:

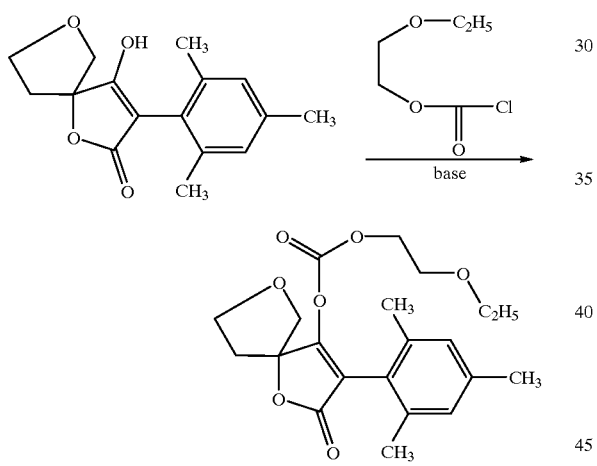

If, in accordance with process (Dα), 3-(2,4,6-trimethylphenyl)-5,5-ethyleneoxaethylene-tetronic acid and methyl chloromonothioformate are used as starting materials, the course of the reaction can be represented as follows:

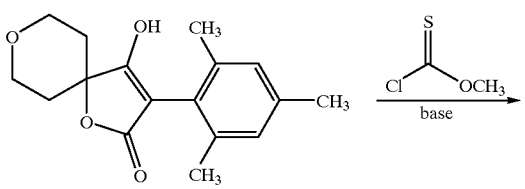

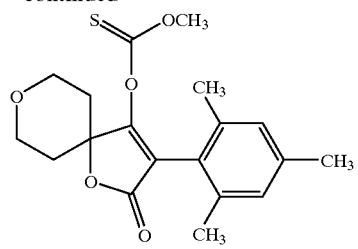

If, in accordance with process (Dβ), 3-(2,4,6-trimethylphenyl)-5,5-ethylenethioethylene-tetronic acid, carbon disulphide and methyl iodide are used as starting components, the course of the reaction can be represented as follows:

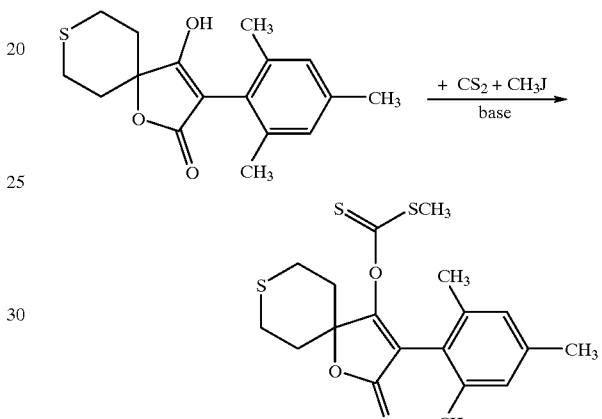

If, in accordance with process (E), 3-(2,4,6-trimethylphenyl)-5,5-methyleneoxapropylene-tetronic acid and methanesulphonyl chloride are used as starting materials, the course of the reaction can be represented by the following equation:

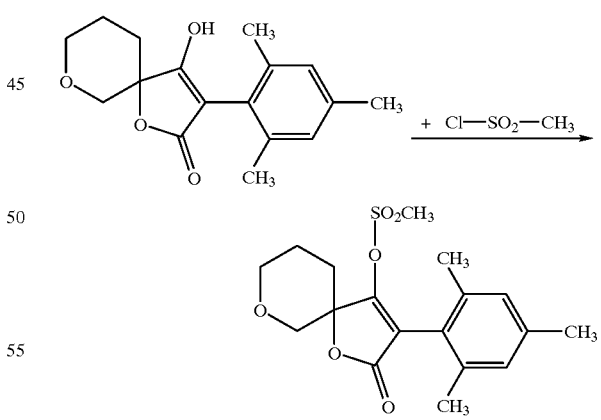

If, in accordance with process (F), 3-(2,4-dimethylphenyl)-5,5-ethylenethioethylene-tetronic acid and 2,2,2-trifluoroethyl chloromethanethio-phosphonate are used as starting materials, the course of the reaction can be represented by the following equation:

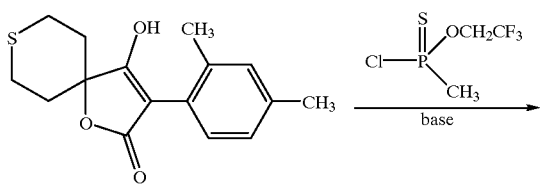
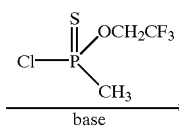

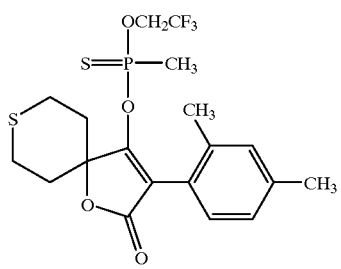

If, in accordance with process (G), 3-(2,4,6-trimethylphenyl)-5,5-ethylene-oxamethylene-tetronic acid and NaOH are used as components, the course of the process according to the invention can be represented by the following equation:

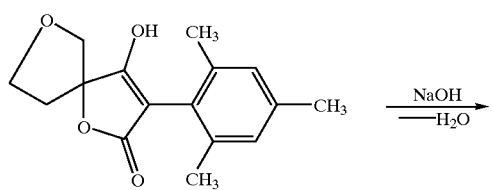

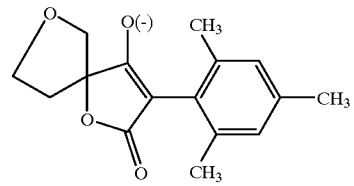

If, in accordance with process (Hα), 3-(2,4,6-trimethylphenyl)-5,5-ethyleneoxaethylene-tetronic acid and ethyl isocyanate are used as starting materials, the course of the reaction can be represented by the following equation:

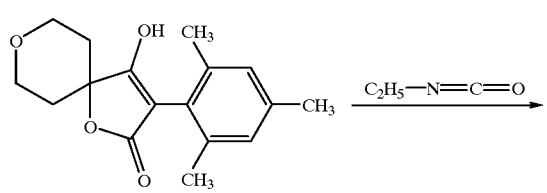
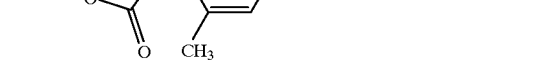

If, in accordance with process (Hβ), 3-(2,4,6-trimethylphenyl)-5,5-(ethyleneacetylamino-ethylene-tetronic acid and dimethylcarbamoyl chloride are used as starting materials, the course of the reaction can be represented by the following equation:

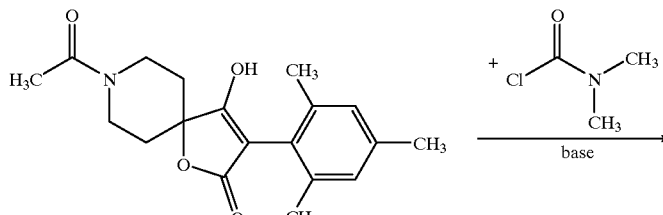
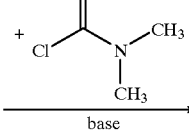

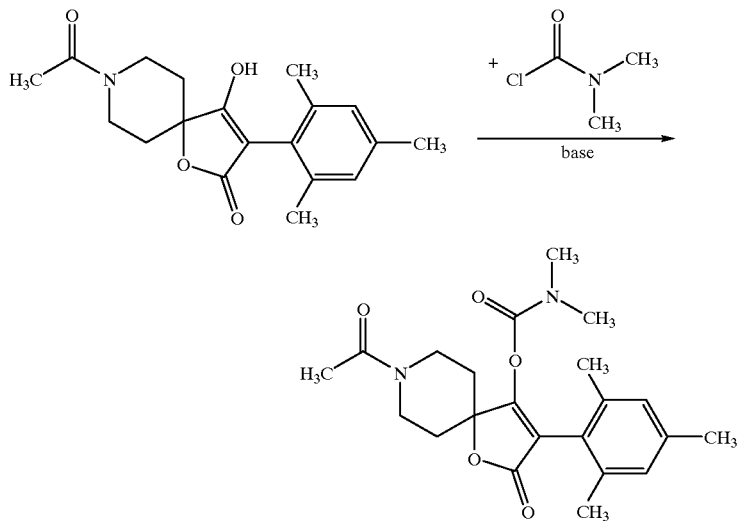

The compounds of the formula (II)

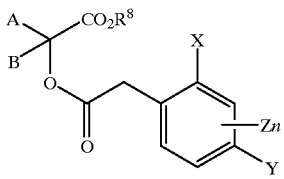

(II)

in which

A, B, X, Y, Z, n and $R^8$ have the abovementioned meanings, which are required as starting substances in the above process (A) are new. The compounds of the formula (II) are obtained, for example, when 2-hydroxycarboxylic acid derivatives of the formula (XIV)

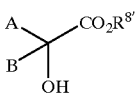

(XIV)

in which $R^{8'}$ represents hydrogen (XIVa) or alkyl (preferably $C_1$–$C_8$-alkyl) (XIVb) and A and B have the abovementioned meanings are acylated with phenylacetyl halides of the formula (XV)

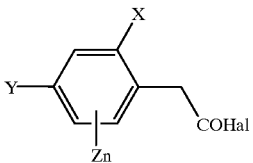

(XV)

in which

X, Y, Z and n have the abovementioned meanings and

Hal represents chlorine or bromine, (Chem. Reviews 52, 237–416 (1953)); and, in the event that $R^{8'}$=hydrogen, the compounds formed, of the formula (IIa)

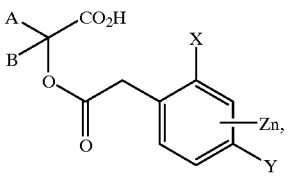

(IIa)

in which

A, B, X, Y, Z and n have the abovementioned meanings, are, if appropriate, esterified (Chem. Ind. (London) 1568 (1968)).

Some of the compounds of the formula (XIV) are known and/or can be prepared by known processes, for example from the cyanohydrins of the formula (XVI)

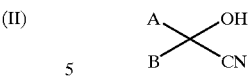

(XVII)

in which

A and B have the abovementioned meanings, [see, for example, Nasarow, Unkowskii, Zh. Obshch. Khim. 26, 3486 (1956) or Bennett, Waddington, J. Chem. Soc. 2831 (1929)].

Some of the compounds of the formula (XVI) are known and/or can be prepared by known methods (for example Eichen, Fritz; Schmidt, Michal; Buchborn, Helga; Arch. Pharm. 320, 348–61, 1987; Sargsyan, M. S.; Ukrtumyan, S. A.; Gevorkyan A. A.; Arm. Khim. Zh 38 494–8, 1985).

The phenylacetyl halides of the formula (XV) are known and/or can be prepared by known methods [see, for example, Lutz, Hinkley, J. Amer. Chem. Soc. 72, 4091 (1950), Harispe, Ann. Chim. (Paris) 11, 6, pp. 249, 282, 283 (1936)].

The acid halides of the formula (III), carboxylic anhydrides of the formula (IV), chloroformic esters or chloroformic thioesters of the formula (V), chloromonothioformic esters or chlorodithioformic esters of the formula (VI), alkyl halides of the formula (VII), sulphonyl chlorides of the formula (VIII), phosphorus compounds of the formula (IX) and metal compounds or amines of the formulae (X) and (XI) and isocyanates of the formula (XII) or carbamoyl chlorides of the formula (XIII), all of which are furthermore required as starting substances for carrying out processes (B), (C), (D), (E), (F), (G) and (H) according to the invention, are generally known compounds of organic or inorganic chemistry.

Process (A) is characterized in that compounds of the formula (II) in which A, B, X, Y, Z, n and $R^8$ have the abovementioned meanings are subjected to an intramolecular condensation reaction in the presence of bases.

Diluents which can be employed in process (A) according to the invention are all inert organic solvents. The following can preferably be used: hydrocarbons, such as toluene and xylene, furthermore ethers, such as dibutyl ether, tetrahydrofuran, dioxane, glycol dimethyl ether and diglycol dimethyl ether, furthermore polar solvents, such as dimethyl sulphoxide, sulpholane, dimethylformamide and N-methyl-pyrrolidone, and also alcohols, such as methanol, ethanol, propanol, isopropanol, butanol, iso-butanol and tert-butanol.

Bases (deprotonating agents) which can be used when carrying out process (A) according to the invention are all customary proton acceptors. The following can preferably be used: the oxides, hydroxides or carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts, such as, for example, triethylbenzylammonium chloride, tetrabutylammonium bromide, ®Adogen 464 (methyltrialkyl($C_8$–$C_{10}$)ammonium chloride) or TDA 1 (tris-(methoxyethoxy-ethyl)-amine).

Alkali metals, such as sodium or potassium, can furthermore be used. Other substances which can be employed are the amides and hydrides of alkali metals and alkaline earth metals, such as sodium amide, sodium hydride and calcium hydride, and furthermore also alkali metal alcoholates, such as sodium methylate, sodium ethylate and potassium tert-butylate.

When carrying out process (A) according to the invention, the reaction temperatures can be varied within a substantial range. In general, the process is carried out at temperatures between –30° C. and 250° C., preferably between 0° C. and 150° C.

Process (A) according to the invention is generally carried out under atmospheric pressure.

When carrying out process (A) according to the invention, the reactant of the formula (II) and the deprotonating base are generally employed in molar amounts. However, it is also possible to use one or the other component in a larger excess (up to 3 mol).

Process (Bα) is characterized in that compounds of the formula (Ia) are reacted with carboxylic acid halides of the formula (III).

Diluents which can be employed in process (Bα) according to the invention are all solvents which are sufficiently inert to acid halides. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, additionally ketones, such as acetone and methyl isopropyl ketone, moreover ethers, such as diethyl ether, tetrahydrofuran and dioxane, and also carboxylic esters, such as ethyl acetate, or else strongly polar solvents, such as dimethyl sulphoxide and sulpholane. If the acid halide is sufficiently stable to hydrolysis, the reaction can also be carried out in the presence of water.

Suitable acid-binding agents for the reaction in accordance with process (Bα) according to the invention are all customary acid acceptors. The following can preferably be used: tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, additionally alkali metal carbonates and alkaline earth metal carbonates, such as sodium carbonate, potassium carbonate and calcium carbonate, and alkali metal hydroxides, such as sodium hydroxide and potassium hydroxide.

When carrying out process (Bα) according to the invention, the reaction temperatures can also be varied within a substantial range. In general, the process is carried out at temperatures between −20° C. and +150° C., preferably between 0° C. and 100° C.

When carrying out process (Bα) according to the invention, the starting substances. of the formula (Ia) and the carboxylic acid halide of the formula (III) are generally used in approximately equivalent amounts. However, it is also possible to employ the carboxylic acid halide in a larger excess (up to 5 mol). Working-up is carried out by customary methods.

Process (Bβ) is characterized in that compounds of the formula (Ia) are reacted with carboxylic anhydrides of the formula (IV).

Diluents which can preferably be used for process (Bβ) according to the invention are those which are also preferably suitable when acid halides are used. Besides, an excess of carboxylic anhydride can also act as the diluent.

When carrying out process (Bβ) according to the invention, the reaction temperatures can be varied within a substantial range. In general, the process is carried out at temperatures between −20° C. and +150° C., preferably between 0° C. and 100° C.

When carrying out process (Bβ) according to the invention, the starting substances of the formula (Ia) and the carboxylic anhydride of the formula (IV) are generally used in approximately equivalent amounts. However, it is also possible to employ the carboxylic anhydride in a larger excess (up to 5 mol). Working-up is carried out by customary methods.

In general, a procedure is followed in which diluent and excess carboxylic anhydride and also the carboxylic acid which forms are removed by distillation or by washing with an organic solvent or with water.

Process (C) is characterized in that compounds of the formula (Ia) are reacted with chloroformic esters or chloroformic thioesters of the formula (V).

Suitable acid-binding agents for the reaction in accordance with process (C) according to the invention are all customary acid acceptors. The following can preferably be used: tertiary amines, such as triethylamine, pyridine, DABCO, DBU, DBA, Hünig base and N,N-dimethylaniline, furthermore alkaline earth metal oxides, such as magnesium oxide and calcium oxide, additionally alkali metal carbonates and alkaline earth metal carbonates, such as sodium carbonate, potassium carbonate and calcium carbonate, and alkali metal hydroxides, such as sodium hydroxide and potassium hydroxide.

Diluents which can be employed in process (C) according to the invention are all solvents which are sufficiently inert to the compounds of the formula (V). The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, additionally ketones, such as acetone and methyl isopropyl ketone, moreover ethers, such as diethyl ether, tetrahydrofuran and dioxane, and also carboxylic esters, such as ethyl acetate, or else strongly polar solvents, such as dimethyl sulphoxide and sulpholane.

When carrying out process (C) according to the invention, the reaction temperatures can be varied within a substantial range. If the process is carried out in the presence of a diluent and of an acid-binding agent, the reaction temperatures are generally between −20° C. and +100° C., preferably between 0° C. and 50° C.

Process (C) according to the invention is generally carried out under atmospheric pressure.

When carrying out process (C) according to the invention, the starting substances of the formula (Ia) and the chloroformic ester, or chloroformic thioester, of the formula (V) are generally employed in approximately equivalent amounts. However, it is also possible to employ one or the other component in a larger excess (up to 2 mol). Working-up is carried out by customary methods. In general, a procedure is followed in which precipitated salts are removed and the remaining reaction mixture is concentrated by stripping off the diluent.

In preparation process (Dα), approximately 1 mol of chloromonothioformic ester, or chlorodithioformic ester, of the formula (VI) is generally reacted per mole of starting compound of the formula (Ia) at 0 to 120° C., preferably at 20 to 60° C.

Suitable diluents which are optionally added are all inert polar organic solvents, such as ethers, carboxylic esters, halogenated hydrocarbons, amides, alcohols, sulphones or sulphoxides.

Substances which are preferably employed are methylene chloride, ethyl acetate, tetrahydrofuran, dimethylformamide or dimethyl sulphoxide.

If, in a preferred embodiment, the enolate salt of the compound of the formula (Ia) is prepared by adding strong deprotonating agents, such as, for example, sodium hydride or potassium tertiary-butylate, a further addition of acid-binding agents can be dispensed with.

If acid-binding agents are employed, then customary inorganic or organic bases are suitable, examples which may be mentioned being sodium hydroxide, sodium carbonate, potassium carbonate, pyridine and triethylamine.

The reaction can be carried out under atmospheric pressure or elevated pressure, preferably under atmospheric pressure. Working-up is carried out by customary methods.

In preparation process (Dβ), the equimolar amount, or an excess, of carbon disulphide is added per mole of starting compound of the formula (Ia). This process is preferably carried out at temperatures from 0 to 50° C., in particular at 20 to 30° C.

Bases which can be employed in process (Dβ) are all customary proton acceptors. Substances which can preferably be used are alkali metal hydrides, alkali metal alcoholates, alkali metal carbonates, alkali metal hydrogen carbonates, alkaline earth metal carbonates or alkaline earth metal hydrogen carbonates or nitrogen bases. Examples which may be mentioned are sodium hydride, sodium methanolate, sodium hydroxide, calcium hydroxide, potassium carbonate, sodium hydrogen carbonate, triethylamine, dibenzyl amine, diisopropylamine, pyridine, quinoline, diazabicyclooctane (DABCO), diazabicyclononene (DBN) and diazabicycloundecene (DBU).

Diluents which can be used in this process are all customary solvents.

The following can preferably be used: aromatic hydrocarbons, such as benzene or toluene, alcohols, such as methanol, ethanol, isopropanol or ethylene glycol, nitriles, such as acetonitrile, ethers, such as tetrahydrofuran or dioxane, amides, such as dimethylformamide, or other polar solvents, such as dimethyl sulphoxide or sulpholane.

Frequently, it appears expedient first to prepare the corresponding salt from the compound of the formula (Ia) by adding a deprotonating agent (such as, for example, potassium tertiary butylate or sodium hydride). The compound (Ia) is reacted with carbon disulphide until the formation of the intermediate compound is complete, for example after stirring at room temperature for several hours.

The further reaction with the alkyl halide of the formula (VII) is preferably carried out at 0 to 70° C., in particular at 20 to 50° C. At least the equimolar amount of alkyl halide is employed for this purpose.

The process is carried out under atmospheric pressure or elevated pressure, preferably under atmospheric pressure.

Again, working-up is carried out by customary methods.

In preparation process (E), approximately 1 mol of sulphonyl chloride (VIII) is reacted per mole of starting compound of the formula (Ia) at 0 to 150° C., preferably at 20 to 70° C.

Suitable diluents which are optionally added are all inert polar organic solvents, such as ethers, carboxylic esters, amides, nitriles, sulphones, sulphoxides or halogenated hydrocarbons, such as methylene chloride.

Substances which are preferably employed are ethyl acetate, tetrahydrofuran, dimethylformamide, dimethyl sulphoxide or methylene chloride.

If, in a preferred embodiment, the enolate salt of the compound of the formula (Ia) is synthesized by adding strong deprotonating agents (such as, for example, sodium hydride or potassium tertiary butylate), the further addition of acid-binding agents can be dispensed with.

If acid-binding agents are employed, then customary inorganic or organic bases are suitable, examples which may be mentioned being sodium hydroxide, sodium carbonate, potassium carbonate, triethylamine and pyridine.

The reaction can be carried out under atmospheric pressure or elevated pressure, preferably under atmospheric pressure. Working-up is carried out by customary methods.

In preparation process (F), 1 to 2 mol, preferably 1 to 1.3 mol, of the phosphorus compound of the formula (IX) to 1 mol of the compound (Ia) are reacted at temperatures between −40° C. and 150° C., preferably between −10 and 110° C., to obtain compounds of the structure (Ie).

Suitable diluents which are optionally added are all inert, polar organic solvents, such as ethers, carboxylic esters, halogenated hydrocarbons, amides, nitriles, sulphides, sulphones, sulphoxides and the like.

Substances which are preferably employed are acetonitrile, ethyl acetate, methylene chloride, tetrahydrofuran, dimethylformamide or dimethyl sulphoxide.

Suitable acid-binding agents which are optionally added are customary inorganic or organic bases, such as hydroxides or carbonates. Examples which may be mentioned are sodium hydroxide, sodium carbonate, potassium carbonate and pyridine.

The reaction can be carried out under atmospheric pressure or under elevated pressure, preferably it is carried out under atmospheric pressure. Working-up is carried out by customary methods of organic chemistry. The end products obtained are preferably purified by crystallization, chromatography or by so-called "incipient distillation", i.e. removal of the volatile components in vacuo.

Process (G) is characterized in that compounds of the formula (Ia) are reacted with metal compounds of the formula (X) or amines of the formula (XI).

Diluents which can be employed for process (G) according to the invention are preferably ethers, such as tetrahydrofuran or dioxane, diethyl ether, or else alcohols, such as methanol, ethanol or isopropanol, but also water. Process (G) according to the invention is generally carried out under atmospheric pressure. The reaction temperatures are generally between −20° C. and 100° C., preferably between 0° C. and 50° C.

In preparation process (Hα), approximately 1 mol of isocyanate of the formula (XII) is reacted per mole of starting compound of the formula (Ia) at 0 to 100° C., preferably 20 to 50° C.

Suitable diluents which are optionally added are all inert organic solvents, such as ethers, aromatic hydrocarbons, carboxylic esters, halogenated hydrocarbons, amides, nitriles, sulphones or sulphoxides.

If appropriate, catalysts may be added to accelerate the reaction. Catalysts which can be employed very advantageously are organotin compounds, such as, for example, dibutyltin dilaurate. The process is preferably carried out under atmospheric pressure.

In preparation process (Hβ), approximately 1 mol of carbamoyl chloride of the formula (XIII) is reacted per mole of starting compound of the formula (Ia) at 0 to 150° C., preferably 20 to 70° C.

Suitable diluents which are optionally added are all inert polar organic solvents, such as ethers, carboxylic esters, halogenated hydrocarbons, amides, alcohols, sulphones or sulphoxides.

Substances which are preferably employed are dimethyl sulphoxide, ethyl acetate, tetrahydrofuran, dimethylformamide or methylene chloride.

If, in a preferred embodiment, the enolate salt of the compound of the formula (Ia) is synthesized by adding strong deprotonating agents (such as, for example, sodium hydride or potassium tertiary butylate), the further addition of acid-binding agents can be dispensed with.

If acid-binding agents are employed, then customary inorganic or organic bases are suitable, examples which may be mentioned being sodium hydroxide, sodium carbonate, potassium carbonate, triethylamine or pyridine.

The active compounds are suitable for combating animal pests, in particular insects, arachnids and nematodes, encountered in agriculture, in forestry, in the protection of stored products and of materials, and in the hygiene field. They can preferably be employed as plant protection agents. They are active against normally sensitive and resistant species and against all or some stages of development. The abovementioned pests include:

From the order of the Isopoda, for example, Oniscus asellus, Armadillidium vulgare and Porcellio scaber.

From the order of the Diplopoda, for example, Blaniulus guttulatus.

From the order of the Chilopoda, for example, Geophilus carpophagus and Scutigera spec..

From the order of the Symphyla, for example, Scutigerella immaculata.

From the order of the Thysanura, for example, Lepisma saccharina.

From the order of the Collembola, for example, Onychiurus armatus.

From the order of the Orthoptera, for example, Blatta orientalis, Periplaneta americana, Leucophaea maderae, Blattella germanica, Acheta domesticus, Gryllotalpa spp., Locusta migratoria migratorioides, Melanoplus differentialis and Schistocerca gregaria.

From the order of the Dermaptera, for example, Forficula auricularia.

From the order of the Isoptera, for example, Reticulitermes spp.

From the order of the Anoplura, for example, Pediculus humanus corporis, Haematopinus spp. and Linognathus spp.

From the order of the Mallophaga, for example, Trichodectes spp. and Damalinea spp.

From the order of the Thysanoptera, for example, Hercinothrips femoralis and Thrips tabaci.

From the order of the Heteroptera, for example, Eurygaster spp., Dysdercus intermedius, Piesma quadrata, Cimex lectularius, Rhodnius prolixus and Triatoma spp.

From the order of the Homoptera, for example, Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus spp., Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp..

From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima and Tortrix viridana.

From the order of the Coleoptera, for example, Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica.

From the order of the Hymenoptera, for example, Diprion spp., Hoplocampa spp., Lasius spp., Monomorium pharaonis and Vespa spp.

From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa.

From the order of the Siphonaptera, for example, Xenopsylla cheopis and Ceratophyllus spp.

From the order of the Arachnida, for example, Scorpio maurus and Latrodectus mactans.

From the order of the Acarina, for example, Acarus siro, Argas spp., Ornithodoros spp., Dermanyssus gallinae, Eriophyes ribis, Phyllocoptruta oleivora, Boophilus spp., Rhipicephalus sp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp.

The compounds of the formula (I) according to the invention are distinguished by a potent insecticidal and acaricidal activity. They are also active against oil insects.

They can be employed particularly successfully against insects which are harmful to plants, such as, for example, against the larvae of the mustard beetle (Phaedon cochleariae) and against the larvae of the green rice leafhopper (Nephotettix cincticeps), or for combating mites which are harmful to plants, such as, for example, against the two-spotted, or greenhouse red, spider mite (Tetranychus urticae).

The active compounds of the formula (I) also have a certain herbicidal action.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is, liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous components in the mixtures are the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxyphenyl)-acetamide; 8-hydroxyquinoline sulphate; methyl (E)-2-{2-[6-(2-cyanophenoxy)pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides:

for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amidosulphuron, bensulphuron-methyl, chlorimuron-ethyl, chlorsulphuron, cinosulphuron, metsulphuron-methyl, nicosulphuron, primisulphuron, pyrazosulphuron-ethyl, thifensulphuron-methyl, triasulphuron and tribenuronmethyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene and stored-product pests, the active compound is distinguished by an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites) such as scaly ticks, Argasidae, scab mites, Trombidae, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenoptes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp., Melophagus spp..

From the order of the Siphonapterida, for example, Pulex spp., Ctenocephalides spp., Xenopsylla spp., Ceratophyllus spp..

From the order of the Heteropterida, for example, Cimex spp., Triatoma spp., Rhodnius spp., Panstrongylus spp.

From the order of the Blattarida, for example, Blatta orientalis, Periplaneta americana, Blattela germanica, Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp., Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp.

For example, they show an outstanding activity against Boophilus microplus, Lucilia cuprina and Musca domestica.

The active compounds of the formula (I) according to the invention are also suitable for combating arthropods which attack agricultural livestock, such as, for example, cattle, sheep, goats, horses, pigs, donkeys, canels, buffalo, rabbits, chickens, turkeys, ducks, geese, honeybees, other domestic animals such as, for example, dogs, cats, cage birds, aquarium fish and so-called experimental animals, such as, for example, hamsters, guinea pigs, rats and mice. By combating these arthropods, it is intended to reduce deaths and reductions in performance (in connection with meat, milk, wool, hides, eggs, honey and the like), so that more economical and simpler animal management is made possible by employing the active compounds according to the invention.

The active compounds according to the invention are used, in the veterinary sector, in a known manner by enteral administration in the form of, for example, tablets, capsules, potions, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration in the form of, for example, bathing or dipping, spraying, pouring on, spotting on, washing, dusting, and with the aid of active-compound-containing shaped articles, such as collars, ear tags, tail marks, limb bands, halters, marking devices and the like.

When used for livestock, poultry, domestic animals and the like, the active compounds of the formula (I) can be used in the form of formulations (for example powders, emulsions, flowables) which comprise 1 to 80% by weight of the active compounds, either directly or after 100- to 10 000-fold dilution, or they can be used in the form of a chemical bath.

Moreover, it has been found that the compounds of the formula (I) according to the invention have a potent insecticidal action against insects which destroy industrial materials.

The following insects may preferably be mentioned by way of example, but not by way of limitation:

Beetles, such as Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lytus planicollis, Lyctus linearis, Lyctus pubescens, Trogoxylon aequale, Minthes rugicollis, Xyleborus spec., Tryptodendron spec., Apate monachus, Bostrychus capucins, Heterobostrychus brunneus, Sinoxylon spec., Dinoderus minutus.

Hymenopterans such as Sirex juvencus, Urocerus gigas, Urocerus gigas taignus, Urocerus augur.

Termites, such as Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.

Bristle tails, such as Lepisma saccharina.

Industrial materials are to be understood as meaning, in the present context, nonliving materials such as, preferably, polymers, glues, sizes, paper and board, leather, wood and derived timber products, and paints.

The material very particularly preferably to be protected against attack by insects is wood and derived timber products.

Wood and derived timber products which can be protected by the composition according to the invention, or by mixtures comprising this composition, are to be understood as meaning, for example, structural timber, wooden beams, railway sleepers, bridge components, jetties, wooden vehicles, boxes, pallets, containers, telegraph poles, wood laggings, windows and doors made of wood, plywood, chipboard, joinery or timber products which are quite generally used in house building or building joinery.

The active compounds can be used as such, in the form of concentrates or in the form of generally customary formulations, such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellent, if appropriate desiccants and UV stabilizers, and if appropriate colourants and pigments and other processing auxiliaries.

The insecticidal compositions or concentrates used for protecting wood and derived timber products comprise the active compound according to the invention in a concentration of 0.0001 to 95% by weight, in particular 0.001 to 60% by weight.

The amount of the compositions or concentrates employed depends on the species and the occurrence of the insects and on the medium. The optimum amount to be employed can in each case be determined by series of tests upon use. However, it is generally sufficient to employ 0.0001 to 20% by weight, preferably 0.001 to 10% by weight, of the active compound based on the material to be protected.

The solvent and/or diluent used is an organic chemical solvent or solvent mixture and/or an oily or oil-like organic chemical solvent or solvent mixture of low volatility and/or a polar organic chemical solvent or solvent mixture and/or water and, if appropriate, an emulsifier and/or wetting agent.

Organic chemical solvents which are preferably employed are oily or oil-like solvents with an evaporation number above 35 and a flash point above 30° C., preferably above 45° C. Such water-insoluble, oily and oil-like solvents of low volatility which are employed are suitable mineral oils or their aromatic fractions, or mineral-oil-comprising solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics with a boiling range of 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-like solvents of low volatility and an evaporation number of above 35 and a flash point of above 30° C., preferably above 45° C., can be replaced in part by organic chemical solvents of high or medium volatility, with the proviso that the solvent mixture also has an evaporation number of above 35 and a flash point of above 30° C., preferably of above 45° C., and that the insecticide/fungicide mixture is soluble or emulsifiable in this solvent mixture.

In a preferred embodiment, part of the organic chemical solvent or solvent mixture is replaced by an aliphatic polar organic chemical solvent or solvent mixture. Substances which are preferably employed are aliphatic organic chemical solvents having hydroxyl and/or ester and/or ether groups, such as, for example, glycol ethers, esters and the like.

Organic chemical binders which are used within the scope of the present invention are the synthetic resins and/or binding drying oils which can be diluted with water and/or dissolved or dispersed or emulsified in the organic chemical solvents employed and which are known per se, in particular binders composed of, or containing, an acrylic resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin used as binder can be employed in the form of an emulsion, dispersion or solution. Bitumen or bituminous substances in amounts of up to 10% by weight may also be used as binders. In addition, colourants, pigments, water repellents, flavour improvers and inhibitors or anticorrosives which are known per se and the like may be used.

According to the invention, the composition or concentrate preferably comprises, as organic chemical binder, at least one alkyd resin or modified alkyd resin and/or a drying vegetable oil. Substances which are preferably used according to the invention are alkyd resins with an oil content of over 45% by weight, preferably 50 to 68% by weight.

Some or all of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of the binder employed).

The plasticizers are from the chemical classes of the phthalic esters, such as dibutyl, dioctyl or benzylbutyl phthalate, phosphoric esters such as tributyl phosphate, adipic esters such as di-(2-ethylhexyl) adipate, stearates such as butyl stearate or amyl stearate, oleates such as butyl oleate, glycerol ethers or higher-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone and ethylenebenzophenone.

Also particularly suitable as a solvent or diluent is water, if appropriate in the form of a mixture with one or more of the abovementioned organic chemical solvents or diluents, emulsifiers and dispersants.

Particularly effective protection of wood is effected by industrial-scale impregnating methods, for example vacuum, double-vacuum or pressure methods.

The ready-to-use compositions can, if appropriate, comprise other insecticides and, if appropriate, also one or more fungicides.

Suitable components which may additionally be admixed are preferably the insecticides and fungicides listed in WO 94/29 268. The compounds mentioned in this document are expressly a component of the present application.

Components which can be very particularly preferably be admixed are insecticides such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides such as epoxyconazole, hexaconazole, azaconazole, propiconazole, tebuconazole, cyproconazole, metconazole, imazalil, dihlofluanid, tolylfluanid, 3-iodo-2-propinyl butylcarbamate, N-octyl-isothiazolin-3-one and 4,5-dichloro-N-octylisothiazolin-3-one.

The preparation and use of the active compounds according to the invention can be seen from the examples which follow.

PREPARATION EXAMPLES

Example (Ia-1)

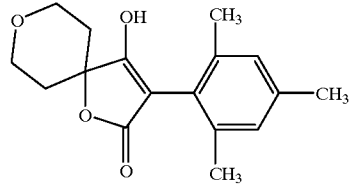

(Ia-1)

67.3 g (0.60 mol) of potassium tert-butylate are introduced into 400 ml of absolute dimethylformamide (DMF), a solution of 133.6 g (0.40 mol) of ethyl 1-(2,4,6-trimethylphenylacetyl-oxy)-4-oxa-cyclohexane-carboxylate is added dropwise at 0 to 10° C., and the mixture is stirred overnight at room temperature.

For working-up, the reaction mixture is slowly added dropwise to 2 l of ice-cooled 1N hydrochloric acid, the precipitate is filtered off with suction and washed thoroughly with water, and the product is dried in a vacuum drying oven.

For purification, the crude product is boiled with n-hexane, again filtered off with suction and dried.

Yield: 91.6 g (79% of theory) of a solid, m.p.: 224–226° C.

The following compounds of the formula (Ia) are obtained analogously or in accordance with the general preparation instructions:

(The following abbreviations are used in the tables:

Me=methyl, Et=ethyl, Pr=propyl, Bu=butyl, Ph=phenyl)

TABLE 5

(Ia)

| Ex. No. | A, B | X | Y | $Z_n$ | M.p. (° C.) |
|---|---|---|---|---|---|
| Ia-2 | —CH$_2$—CH(CH$_3$)—O—(CH$_2$)$_2$— | Me | Me | 6-Me | 235 |
| Ia-3 | —CH$_2$—CH(CH$_3$)—O—(CH$_2$)$_2$— | Me | Me | H | |
| Ia-4 | —CH$_2$—CH(CH$_3$)—O—(CH$_2$)$_2$— | Cl | Cl | H | |
| Ia-5 | —CH$_2$—CH(CH$_3$)—O—(CH$_2$)$_2$— | Cl | H | Cl | |
| Ia-6 | —CH$_2$—CH(C$_2$H$_5$)—O—(CH$_2$)$_2$— | Me | Me | 6-Me | oil |
| Ia-7 | —CH$_2$—CH(C$_2$H$_5$)—O—(CH$_2$)$_2$— | Me | Me | H | |
| Ia-8 | —CH$_2$—CH(C$_2$H$_5$)—O—(CH$_2$)$_2$— | Cl | Cl | H | |
| Ia-9 | —CH$_2$—CH(C$_2$H$_5$)—O—(CH$_2$)$_2$— | Cl | H | Cl | |
| Ia-10 | —CH$_2$—C(CH$_3$)$_2$—O—(CH$_2$)$_2$— | Me | Me | 6-Me | |
| Ia-11 | —CH$_2$—C(CH$_3$)$_2$—O—(CH$_2$)$_2$— | Me | Me | H | |
| Ia-12 | —CH$_2$—C(CH$_3$)$_2$—O—(CH$_2$)$_2$— | Cl | Cl | H | |
| Ia-13 | —CH$_2$—C(CH$_3$)$_2$—O—(CH$_2$)$_2$— | Cl | H | 6-Cl | |
| Ia-14 | —CH$_2$—CH(Me)—O—CH(Me)—CH$_2$— | Me | Me | 6-Me | |
| Ia-15 | —CH$_2$—CH(Me)—O—CH(Me)—CH$_2$— | Me | Me | H | |
| Ia-16 | —CH$_2$—CH(Me)—O—CH(Me)—CH$_2$— | Cl | Cl | H | |
| Ia-17 | —CH$_2$—CH(Me)—O—CH(Me)—CH$_2$— | Cl | H | Cl | |
| Ia-18 | —CH$_2$O—(CH$_2$)$_3$— | Me | Me | 6-Me | |
| Ia-19 | —CH$_2$—O—CH(Me)—(CH$_2$)$_2$— | Me | Me | -Me | |

TABLE 5-continued (Ia)

| Ex. No. | A, B | X | Y | $Z_n$ | M.p. (° C.) |
|---|---|---|---|---|---|
| Ia-20 | —CH$_2$—O—(CH$_2$)$_2$— | Me | Me | 6-Me | |
| Ia-21 | —CH(Me)—O—(CH$_2$)$_2$— | Me | Me | 6-Me | |
| Ia-22 | —CH$_2$—O—CH(Me)—CH$_2$— | Me | Me | 6-Me | |
| Ia-23 | —CH$_2$—O—CH$_2$—CH(Me)— | Me | Me | 6-Me | |
| Ia-24 | —(CH$_2$)$_2$—S—(CH$_2$)$_2$— | Me | Me | 6-Me | 266–267 |
| Ia-25 | —(CH$_2$)$_2$—S—(CH$_2$)$_2$— | Me | Me | H | |
| Ia-26 | —(CH$_2$)$_2$—S—(CH$_2$)$_2$— | Cl | Cl | H | |
| Ia-27 | —CH$_2$—CH(CH$_3$)—S—(CH$_2$)$_2$— | Me | Me | 6-Me | |
| Ia-28 | —CH$_2$—CH(CH$_3$)—S—(CH$_2$)$_2$— | Me | Me | H | |
| Ia-29 | —CH$_2$—CH(CH$_3$)—S—(CH$_2$)$_2$— | Cl | Cl | H | |
| Ia-30 | —CH$_2$—S—(CH$_2$)$_2$— | Me | Me | 6-Me | 122–124 |
| Ia-31 | —CH$_2$—S—(CH$_2$)$_2$— | Me | Me | H | |
| Ia-32 | —CH$_2$—S—(CH$_2$)$_2$— | Cl | Cl | H | |
| Ia-33 | —(CH$_2$)$_2$—N(COMe)—(CH$_2$)$_2$— | Me | Me | 6-Me | 230 |
| Ia-34 | —(CH$_2$)$_2$—N(COMe)—(CH$_2$)$_2$— | Me | Me | H | |
| Ia-35 | —(CH$_2$)$_2$—N(COMe)—(CH$_2$)$_2$— | Cl | Cl | H | |
| Ia-36 | —(CH$_2$)$_2$—O—(CH$_2$)$_2$— | Me | H | 6-Me | |
| Ia-37 | —(CH$_2$)$_2$—O—(CH$_2$)$_2$— | Cl | Me | H | 219 |
| Ia-38 | —(CH$_2$)$_2$—O—(CH$_2$)$_2$— | Me | Cl | H | |
| Ia-39 | —(CH$_2$)$_2$—O—(CH$_2$)$_2$— | Cl | OMe | H | |
| Ia-40 | —(CH$_2$)$_2$—O—(CH$_2$)$_2$— | Me | Ome | H | |
| Ia-41 | —(CH$_2$)$_2$—O—(CH$_2$)$_2$— | Me | H | 6-OMe | |

Example (Ib-1)

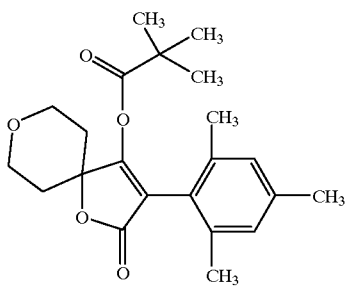

(Ib-1)

28.8 g (0.10 mol) of 3-(2,4,6-trimethylphenyl)-5,5-ethylene-oxa-ethylenetetronic acid of Example (Ia-1) are introduced into 400 ml of absolute methylene chloride, 15.2 g (0.15 mol) of triethylamine are added, a solution of 15.7 g (0.13 mol) of pivaloyl chloride is added dropwise at 0 to 10° C., and the mixture is stirred for a few hours at room temperature.

For working-up, the reaction mixture is washed in succession with 10% strength citric acid, sodium hydrogen carbonate solution and water, and the organic phase is dried over sodium sulphate and evaporated.

For purification, the crude product is stirred with petroleum ether and filtered off with suction.

Yield: 29.4 g (78% of theory) of a solid; m.p.: 119–120° C.

The following compounds of the formulae (Ib) to (Ig) are obtained analogously or following the general preparation instructions:

TABLE 6

(Ib)

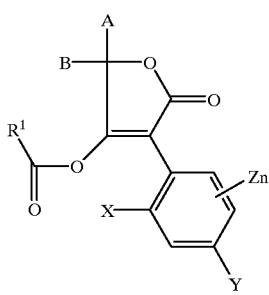

| Ex. No. | A, B | X | Y | $Z_n$ | $R^1$ | M.p. (° C.) |
|---|---|---|---|---|---|---|
| Ib-2 | —(CH$_2$)$_2$—O—(CH$_2$)$_2$— | Me | Me | 6-Me | i-Pr | 122 |
| Ib-3 | —(CH$_2$)$_2$—O—(CH$_2$)$_2$— | Me | Me | 6-Me | CMe$_2$—CH$_2$Cl | 170 |
| Ib-4 | —(CH$_2$)$_2$—O—(CH$_2$)$_2$— | Me | Me | 6-Me | CMe$_2$-i-Pr | 118 |
| Ib-5 | —(CH$_2$)$_2$—O—(CH$_2$)$_2$— | Me | Me | 6-Me | CH=CMe$_2$ | 139 |

TABLE 6-continued

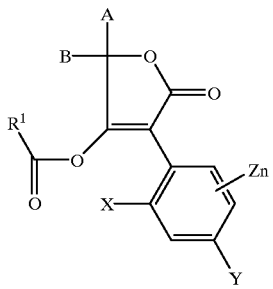

(Ib)

| Ex. No. | A, B | X | Y | $Z_n$ | $R^1$ | M.p. (° C.) |
|---|---|---|---|---|---|---|
| Ib-6 | —(CH$_2$)$_2$—O—(CH$_2$)$_2$— | Me | Me | 6-Me | Ph | 147–53 |
| Ib-7 | —(CH$_2$)$_2$—O—(CH$_2$)$_2$— | Me | Me | 6-Me | CMe$_2$—CH$_2$F | 153–55 |
| Ib-8 | —(CH$_2$)$_2$—O—(CH$_2$)$_2$— | Me | Me | 6-Me | CMe(CH$_2$F)$_2$ | 158 |
| Ib-9 | —(CH$_2$)$_2$—O—(CH$_2$)$_2$— | Me | Me | 6-Me | CMe(CH$_2$Cl)$_2$ | 188 |
| Ib-10 | —(CH$_2$)$_2$—O—(CH$_2$)$_2$— | Me | Me | 6-Me | C(CH$_2$Cl)$_3$ | 177 |
| Ib-11 | —(CH$_2$)$_2$—O—(CH$_2$)$_2$— | Me | Me | 6-Me | CMe$_2$—CH$_2$OMe | 177 |
| Ib-12 | —(CH$_2$)$_2$—O—(CH$_2$)$_2$— | Me | Me | 6-Me | CMe(CH$_2$OMe)$_2$ | 104 |
| Ib-13 | —(CH$_2$)$_2$—O—(CH$_2$)$_2$— | Me | Me | 6-Me | C(CH$_2$OMe)$_3$ | 103 |
| Ib-14 | —(CH$_2$)$_2$—O—(CH$_2$)$_2$— | Me | Me | 6-Me | CMe(—CH$_2$—)$_5$ | 157 |
| Ib-15 | —(CH$_2$)$_2$—O—(CH$_2$)$_2$— | Me | Me | 6-Me | CMe(CH$_2$OCH$_2$OCH$_2$) | 176–79 |
| Ib-16 | —(CH$_2$)$_2$—O—(CH$_2$)$_2$— | Me | Me | 6-Me | (CH$_2$)$_8$—CH$_3$ | oil |
| Ib-17 | —(CH$_2$)$_2$—O—(CH$_2$)$_2$— | Me | Me | 6-Me | (CH$_2$)$_{14}$—CH$_3$ | oil |
| Ib-18 | —(CH$_2$)$_2$—O—(CH$_2$)$_2$— | Cl | Cl | H | Me | |
| Ib-19 | —(CH$_2$)$_2$—O—(CH$_2$)$_2$— | Me | Me | H | i-Pr | |
| Ib-20 | —CH$_2$—CH(Me)—O—(CH$_2$)$_2$— | Me | Me | 6-Me | i-Pr | |
| Ib-21 | —CH$_2$—CH(Me)—O—(CH$_2$)$_2$— | Me | Me | 6-Me | CH$_2$-t-Bu | |
| Ib-22 | —CH$_2$—CH(Me)—O—(CH$_2$)$_2$— | Me | Me | 6-Me | t-Bu | 130 |
| Ib-23 | —CH$_2$—CH(Me)—O—(CH$_2$)$_2$— | Me | Me | 6-Me | CMe$_2$—CH$_2$Cl | |
| Ib-24 | —CH$_2$—CH(Me)—O—CH(Me)—CH$_2$— | Me | Me | 6-Me | t-Bu | |
| Ib-25 | —CH$_2$—CH(Et)—O—CH(Me)—CH$_2$— | Me | Me | 6-Me | t-Bu | |
| Ib-26 | —CH$_2$—C(CH$_3$)$_2$—O—(CH$_2$)$_2$— | Me | Me | 6-Me | t-Bu | |
| Ib-27 | —CH$_2$—O—(CH$_2$)$_3$— | Me | Me | 6-Me | t-Bu | |
| Ib-28 | —CH$_2$—O—CH(Me)—(CH$_2$)$_2$— | Me | Me | 6-Me | t-Bu | |
| Ib-29 | —CH$_2$—O—(CH$_2$)$_2$— | Me | Me | 6-Me | t-Bu | |
| Ib-30 | —(CH$_2$)$_2$—S—(CH$_2$)$_2$— | Me | Me | 6-Me | Me | 198–200 |
| Ib-31 | —(CH$_2$)$_2$—S—(CH$_2$)$_2$— | Me | Me | 6-Me | t-Bu | 113–115 |
| Ib-32 | —CH$_2$—S—(CH$_2$)$_2$— | Me | Me | 6-Me | Me | oil |
| Ib-33 | —CH$_2$—S—(CH$_2$)$_2$— | Me | Me | 6-Me | i-Pr | 108–110 |
| Ib-34 | —CH$_2$—S—(CH$_2$)$_2$— | Me | Me | 6-Me | t-Bu | 95–97 |
| Ib-35 | —(CH$_2$)$_2$—N(COMe)—(CH$_2$)$_2$— | Me | Me | 6-Me | t-Bu | 68 |
| Ib-36 | —(CH$_2$)$_2$—O—(CH$_2$)$_2$— | Me | Me | 6-Me | CH$_2$—CF═CF$_2$ | oil |
| Ib-37 | —(CH$_2$)$_2$—O—CHEt—CH$_2$— | Me | Me | 6-Me | t-Bu | 132 |
| Ib-38 | —(CH$_2$)$_2$—O—CHEt—CH$_2$— | Me | Me | 6-Me | CH$_2$-t-Bu | 69 |
| Ib-39 | —(CH$_2$)$_2$—O—(CH$_2$)$_2$— | Me | Me | 6-Me | 4-NO$_2$—Ph— | 191–195 |
| Ib-40 | —(CH$_2$)$_2$—O—(CH$_2$)$_2$— | Me | Me | 6-Me | 4-OIMe—Ph— | 112–116 |
| Ib-41 | —(CH$_2$)$_2$—O—(CH$_2$)$_2$— | Me | Me | 6-Me | CMe$_2$Et | 130–132 |
| Ib-42 | —(CH$_2$)$_2$—O—(CH$_2$)$_2$— | Me | Me | 6-Me | CMe$_2$CH$_2$OEt | 126–129 |
| Ib-43 | —(CH$_2$)$_2$—O—(CH$_2$)$_2$— | Me | H | 6-Me | t-Bu | |
| Ib-44 | —(CH$_2$)$_2$—O—(CH$_2$)$_2$— | Cl | Me | H | t-Bu | 128 |
| Ib-45 | —(CH$_2$)$_2$—O—(CH$_2$)$_2$— | Me | Cl | H | t-Bu | |
| Ib-46 | —(CH$_2$)$_2$—O—(CH$_2$)$_2$— | Cl | OMe | H | t-Bu | |
| Ib-47 | —(CH$_2$)$_2$—O—(CH$_2$)$_2$— | Me | OMe | H | t-Bu | |
| Ib-48 | —(CH$_2$)$_2$—O—(CH$_2$)$_2$— | Me | H | 6-OMe | t-Bu | |

TABLE 7

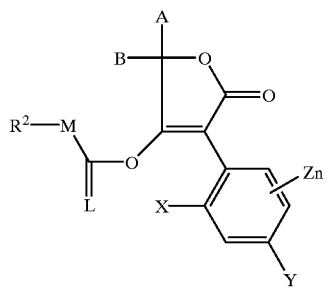
(Ic)

| Ex. No. | A, B | X | Y | $Z_n$ | L | M | $R^2$ | M.p. (° C.) |
|---|---|---|---|---|---|---|---|---|
| Ic-1 | —(CH$_2$)$_2$—O—(CH$_2$)$_2$— | Me | Me | 6-Me | O | O | i-Pr | 104–05 |
| Ic-2 | —(CH$_2$)$_2$—O—(CH$_2$)$_2$— | Me | Me | 6-Me | O | O | t-Bu | 107 |
| Ic-3 | —CH$_2$—CH(Me)—O—(CH$_2$)$_2$— | Me | Me | 6-Me | O | O | i-Pr | oil |
| Ic-4 | —CH$_2$—CH(Me)—O—CH(Me)—CH$_2$— | Me | Me | 6-Me | O | O | s-Bu | |
| Ic-5 | —CH$_2$—C(CH$_3$)$_2$—O—(CH$_2$)$_2$— | Me | Me | 6-Me | O | O | i-Pr | |
| Ic-6 | —CH$_2$—S—(CH$_2$)$_2$— | Me | Me | 6-Me | O | O | i-Pr | 119–121 |
| Ic-7 | —(CH$_2$)$_2$—O—(CH$_2$)$_2$— | Me | Me | 6-Me | O | O | CH$_2$ t-Bu | 145–147 |
| Ic-8 | —(CH$_2$)$_2$—O—(CH$_2$)$_2$— | Me | Me | 6-Me | O | O | i-Bu | 96–98 |
| Ic-9 | —(CH$_2$)$_2$—O—(CH$_2$)$_2$— | Me | Me | 6-Me | O | O | s-Bu | 111–113 |
| Ic-10 | —(CH$_2$)$_2$—O—(CH$_2$)$_2$— | Me | Me | 6-Me | O | S | i-Pr | 103–105 |

TABLE 8

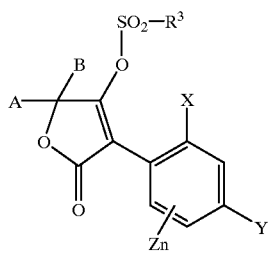
(Id)

| Ex. No. | A | B | X | Y | Z | $R^3$ | M.p. ° C. |
|---|---|---|---|---|---|---|---|
| Id-1 | —(CH$_2$)$_2$—O—(CH$_2$)$_2$— | | Me | Me | 6-Me | Me | 171–173 |
| Id-2 | —(CH$_2$)$_2$—O—(CH$_2$)$_2$— | | Me | Me | 6-Me | 4-Me—Ph— | 146–148 |

Example for the preparation of an intermediate of the formula (II):

Example (II-1)

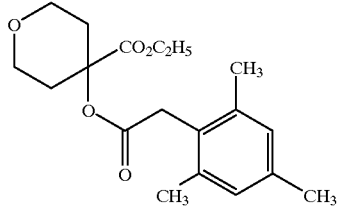
(II-1)

31.3 g (0.18 mol) of ethyl 1-hydroxy-4oxa-cyclohexanecarboxylate are introduced into 150 ml of methylene chloride, 21.9 g (0.216 mol) of triethylamine are added, a solution of 38.9 g (0.20 mol) of mesitylacetyl chloride in 50 ml of methylene chloride is added dropwise at 0 to 10° C., and the mixture is stirred overnight at room temperature.

For working-up, the reaction mixture is washed in succession with 10% strength citric acid, sodium hydrogen carbonate solution and water, and the organic phase is dried over magnesium sulphate and evaporated.

Yield: 60.6 g of an oil (quantitative).

The following compounds of the formula (II) are obtained analogously or in accordance with the general preparation instructions:

TABLE 9

(II)

| Ex. No. | A, B | X | Y | $Z_n$ | $R^8$ | M.p. (° C.) |
|---|---|---|---|---|---|---|
| II-2 | —CH$_2$—CH(Me)—O—(CH$_2$)$_2$— | Me | Me | 6-Me | Et | oil |
| II-3 | —(CH$_2$)$_2$—S—(CH$_2$)$_2$— | Me | Me | 6-Me | Et | oil |
| II-4 | —CH$_2$—S—(CH$_2$)$_2$— | Me | Me | 6-Me | Et | oil |
| II-5 | —(CH$_2$)$_2$—O—CHMe—CH$_2$— | Me | Me | 6-Me | Et | oil |
| II-6 | —(CH$_2$)$_2$—O—CHEt—CH$_2$— | Me | Me | 6-Me | Et | oil |
| II-7 | —(CH$_2$)$_2$—(N—COMe)—(CH$_2$)$_2$— | Me | Me | 6-Me | Et | oil |

Example (XIV-1)

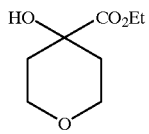

A mixture of 130 g (approximately 1 mol) of 4-hydroxy-tetrahydropyran-4-carbonitrile and 1050 ml of dry ethanol is saturated with hydrochloric acid at −20° C. to 0° C. The mixture is allowed to come to room temperature, excess HCl is removed, the mixture is concentrated in vacuo, 1.5 l of water are added, and the mixture is stirred for 3 hours at room temperature. It is filtered and extracted twice using methylene chloride. After the solvent has been removed, 118 g (61% of theory) of ethyl 4-hydroxy-tetrahydropyran-4-carboxylate of b.p.$_{0.1}$ 65° C. are obtained.

The following comparison compounds which are known from the prior art were employed in the use examples:

(A)

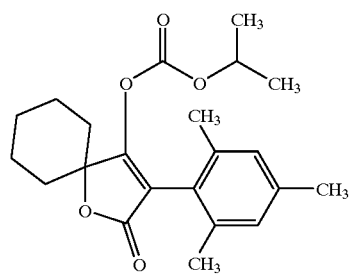

(B)

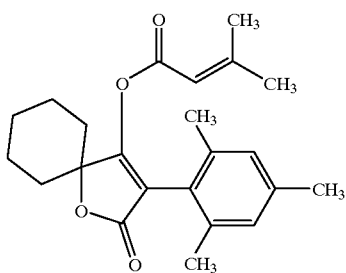

(all disclosed in EP-528 156)

Example A

Myzus test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) which are severely infested with the peach aphid (Myzus persicae) are treated by being dipped into the preparation of active compound of the desired concentration.

After the specified period of time, the destruction in % is determined. 100% means that all the aphids have been killed; 0% means that none of the aphids have been killed.

In this test, a destruction of at least 95% was caused, after 6 days, for example, by the compounds of Preparation Examples Ia-1, Ib-1, Ib-12, Ib-15 and Ic-1 at an exemplary active compound concentration of 0.1%, while the prior-art compound (B) only caused a destruction of 70% at an active compound concentration of 0.1%.

Example B

Critical concentration test/root-systemic action
Test insect: Aphis fabae
Solvent: 4 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

The preparation of active compound is intimately mixed with the soil. The concentration of the active compound in the preparation is of practically no importance here, only the amount by weight of active compound per unit volume of soil, which is given in ppm (=mg/l), being decisive. The treated soil is transferred into pots and these are planted with broad beans (Vicia faba). The active compound can in this way be taken up from the soil by the roots of the plants and be transported into the leaves.

To demonstrate the root-systemic effect, the leaves are infested with the abovementioned test animals after 8 days. After a further 6 days, the evaluation is made by counting or estimating the dead animals. The root-systemic action of the active compound is deduced from the mortality figures. It is 100% if all the test animals have been killed and 0% if just as many test insects are still alive as in the case of the untreated control.

In this test, an activity of 100% was shown, for example, by the compounds of Preparation Examples Ia-1, Ib-2, Ib-5, Ib-7, Ib-8, Ib-12, Ib-15, Ib-16, Ib-17 and Ic-2 at an exemplary active compound concentration of 200 ppm.

Example C

Nephotettix test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with emulsifier-containing water to the desired concentration.

Rice seedlings (Oryza sativa) are treated by being dipped into the preparation of active compound of the desired concentration and are infested with larvae of the green rice leafhopper (Nephotettix cincticeps) while the seedlings are still moist.

After the specified period of time, the destruction in % is determined. 100% means that all the leafhoppers have been killed; 0% means that none of the leafhoppers have been killed.

In this test, a destruction of 100% was shown, after 6 days, for example, by the compounds of Preparation Examples Ia-1, Ib-1, Ib-16, Ic-1 and Ic-3 at an exemplary active compound concentration of 0.01%, while the known compound (A) caused no destruction.

Example D

Tetranychus test (OP resistant)
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which are severely infested with all development stages of the two-spotted spider mite (Tetranychus urticae) are sprayed with a preparation of active compound of the desired concentration.

After the specified period of time, the destruction in % is determined. 100% means that all the spider mites have been killed; 0% means that none of the spider mites have been killed.

In this test, for example, the compounds of Preparation Examples Ia-1, Ia-24, Ib-1, Ib-2, Ib-16, Ib-31 and Ic-1 showed a destruction of at least 95% after 7 days at an exemplary active compound concentration of 0.02% and the compounds of Preparation Examples Ib-5, Ib-7, Ib-11 and Ib-22 showed a destruction of at least 98% after 7 days at an exemplary active compound concentration of 0.1%.

Example E

Panonychus test
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with emulsifier-containing water to the desired concentration.

Plum trees (Prunus domestica) approximately 30 cm in height which are severely infested with all development stages of the fruit tree red spider mite (Panonychus ulmi) are sprayed with a preparation of active compound of the desired concentration.

After the specified period of time, the destruction in % is determined. 100% means that all the spider mites have been killed; 0% means that none of the spider mites have been killed.

In this test, for example, the compounds of Preparation Examples Ia-1, Ia-24, Ib-1, Ib-2, Ib-16, Ib-31 and Ic-1 caused a destruction of at least 95% after 7 days at an exemplary active compound concentration of 0.02%.

Example F

Fly larvae test/development-inhibitory action

Test animals: All larval stages of Lucilia cuprina (OP resistant) [pupae and adults (without contact with the active compound)]

Solvent: 35 parts by weight of ethylene glycol monomethyl ether
35 parts by weight of nonylphenol glycol ether To prepare a suitable formulation, three parts by weight of active compound are mixed with seven parts of the above-mentioned solvent/emulsifier mixture, and the resulting emulsion concentrate is diluted with water to the concentration desired in each case.

For each concentration, 30 to 50 larvae are transferred to horsemeat (1 cm$^3$) in glass tubes, onto which 500 $\mu$l of the dilution to be tested are pipetted. The glass tubes are placed into plastic beakers whose bottom is covered with seasand and kept in a controlled-environment cabin (26° C.±1.5° C., relative humidity 70%±10%). The activity is checked after 24 hours and 48 hours (larvicidal action). After the larvae have left (approximately 72 hours), the glass tubes are removed, and perforated plastic lids pressed on to the beakers. After 1½ times the development time (hatching of the control flies), the hatched flies and the pupae/puparia are counted.

The criterion for the action is defined as the occurrence of death in the treated larvae after 48 hours (larvicidal effect) or the inhibition of adults hatching from the pupae or the inhibition of pupation. The criterion for in-vitro action of a substance is defined as the inhibition of fly development or a standstill of the development prior to the adult stage. 100% larvicidal action means that all the larvae have died after 48 hours. 100% development-inhibitory action means that no adult flies have hatched.

In this test, for example, the compounds of Preparation Examples Ia-2, Ia-24, Ib-4, Ib-15, Ib-22, Ib-24 and Ib-30 showed an action of in each case 100% at an exemplary active compound concentration of 1000 ppm.

What is claimed is:

1. Compounds of the formula (II)

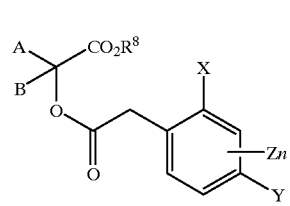

(II)

in which

R$^8$ represents alkyl;

A and B represent $C_1$–$C_6$-alkanediyl which is optionally monosubstituted or polysubstituted by identical or different substituents selected from the group consisting of halogen, $C_1$–$C_8$-alkyl, $C_3$–$C_8$-cycloalkyl, $C_1$–$C_8$-halogenoalkyl, $C_1$–$C_6$-alkoxy, $C_1$–$C_6$-alkylthio or phenyl and in which one or two carbon atoms which are not directly adjacent are replaced by the group

or oxygen or sulphur,

X represents $C_1$–$C_6$-alkyl, halogen or $C_1$–$C_6$-alkoxy,

Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, and n represents 0, 1 or 2 and wherein R represents hydrogen, Q, COQ or CO Q and Q represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$ alkyl, each of which is optionally monosubstituted or polysubstituted by halogen, or represents $C_3$–$C_8$-cycloalkyl which is optionally monosubstituted or polysubstituted by halogen, $C_1$–$C_4$-alkyl or $C_1$–$C_4$-alkoxy, or represents phenyl or benzyl, each of which is optionally monosubstituted to trisubstituted by halogen, nitro, $C_1$–$C_6$-alkyl, $C_1$–$C_6$-alkoxy or $C_1$–$C_6$-halogenoalkyl.

2. Process for the preparation of compounds of the formula (II) according to claim 1 wherein 2-hydroxycarboxylic acid derivatives of the formula (XIV)

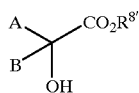

(XIV)

in which $R^{8'}$ represents hydrogen or alkyl and

A and B have the meanings given in claim 1, are acylated with phenylacetyl halides of the formula (XV)

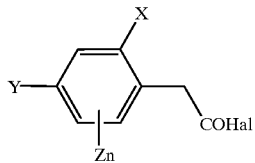

(XV)

in which

X, Y, Z and n have the meanings given in claim 1 and

Hal represents chlorine or bromine, and, in the event that $R^{8'}$=hydrogen, the compounds formed, of the formula (IIa)

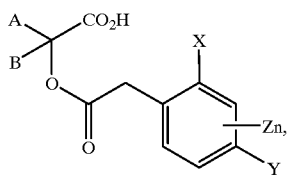

(IIa)

in which

A, B, X, Y, Z and n have the abovementioned meanings, are, optionally, esterified.

* * * * *